United States Patent
Hazard et al.

(10) Patent No.: US 7,353,056 B2
(45) Date of Patent: Apr. 1, 2008

(54) OPTIMIZED SWITCHING CONFIGURATIONS FOR RECONFIGURABLE ARRAYS OF SENSOR ELEMENTS

(75) Inventors: Christopher Robert Hazard, Niskayuna, NY (US); Robert Gideon Wodnicki, Niskayuna, NY (US); Rayette Ann Fisher, Niskayuna, NY (US); Kai E. Thomenius, Clifton Park, NY (US); Lowell Scott Smith, Niskayuna, NY (US); David Martin Mills, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 443 days.

(21) Appl. No.: 10/978,175

(22) Filed: Oct. 29, 2004

(65) Prior Publication Data

US 2005/0096546 A1    May 5, 2005

Related U.S. Application Data

(63) Continuation-in-part of application No. 10/383,990, filed on Mar. 6, 2003, now Pat. No. 6,865,140.

(51) Int. Cl.
*A61B 5/05*    (2006.01)
*A61B 8/00*    (2006.01)

(52) U.S. Cl. ........................ 600/407; 600/447

(58) Field of Classification Search ................ 600/407, 600/409, 437, 443, 447; 73/625–626; 703/4, 703/14, 19; 706/14, 24, 911, 924; 716/1–6
See application file for complete search history.

(56) References Cited

U.S. PATENT DOCUMENTS

| | | | |
|---|---|---|---|
| 4,164,213 A | * | 8/1979 | Hoelzler ...................... 600/447 |
| 4,215,584 A | * | 8/1980 | Kuroda et al. ................ 73/626 |
| 4,307,613 A | | 12/1981 | Fox |
| 4,641,660 A | | 2/1987 | Bele |
| 4,890,267 A | | 12/1989 | Rudolph |
| 5,146,435 A | | 9/1992 | Bernstein |

(Continued)

FOREIGN PATENT DOCUMENTS

EP    0 040 375 A1    11/1981

(Continued)

OTHER PUBLICATIONS

Ladabaum et al., Surface Micromachined Capacitive Ultrasonic Transducers, IEEE Trans. Ultrasonics, Ferroelectrics, and Frequency Control, vol. 45, No. 3, May 1998, pp. 678-690.

(Continued)

Primary Examiner—Francis J. Jaworski
(74) Attorney, Agent, or Firm—Fletcher Yoder

(57) ABSTRACT

The reconfigurable ultrasound array disclosed herein is one that allows groups of subelements to be connected together dynamically so that the shape of the resulting element can be made to match the shape of the wave front. This can lead to improved performance and/or reduced channel count. Reconfigurability can be achieved using a switching network. A methodology and an algorithm are disclosed that allows the performance of this switching network to be improved by properly choosing the configuration of the switching network.

33 Claims, 16 Drawing Sheets

U.S. PATENT DOCUMENTS

| | | |
|---|---|---|
| 5,452,268 A | 9/1995 | Bernstein |
| 5,558,623 A | 9/1996 | Cody |
| 5,569,968 A | 10/1996 | Lal et al. |
| 5,596,222 A | 1/1997 | Bernstein |
| 5,619,476 A | 4/1997 | Haller et al. |
| 5,684,324 A | 11/1997 | Bernstein |
| 5,732,706 A | 3/1998 | White et al. |
| 5,774,690 A * | 6/1998 | O'Neill .................. 716/9 |
| 5,870,351 A | 2/1999 | Ladabaum et al. |
| 5,894,452 A | 4/1999 | Ladabaum et al. |
| 5,902,241 A | 5/1999 | Seyed-Bolorforosh et al. |
| 5,982,709 A | 11/1999 | Ladabaum et al. |
| 6,004,832 A | 12/1999 | Haller et al. |
| 6,120,449 A | 9/2000 | Snyder et al. |
| 6,282,963 B1 * | 9/2001 | Haider .................. 73/602 |
| 6,292,435 B1 | 9/2001 | Savord et al. |
| 6,320,239 B1 | 11/2001 | Eccardt et al. |
| 6,325,757 B1 | 12/2001 | Erikson et al. |
| 6,328,697 B1 | 12/2001 | Fraser |
| 6,359,367 B1 | 3/2002 | Sumanaweera et al. |
| 6,381,197 B1 | 4/2002 | Savord et al. |
| 6,384,516 B1 | 5/2002 | Fraser |
| 6,434,539 B1 * | 8/2002 | Woodsum et al. ............ 706/13 |
| 6,443,901 B1 | 9/2002 | Fraser |
| 6,461,299 B1 | 10/2002 | Hossack |
| 6,503,204 B1 | 1/2003 | Sumanaweera et al. |
| 6,571,445 B2 | 6/2003 | Ladabaum |
| 6,585,653 B2 | 7/2003 | Miller |
| 6,589,180 B2 | 7/2003 | Erikson et al. |
| 6,736,779 B1 | 5/2004 | Sano et al. |
| 6,754,241 B1 * | 6/2004 | Krishnamurthy et al. ... 370/537 |
| 6,768,713 B1 * | 7/2004 | Siala et al. .................. 370/203 |
| 6,551,248 B2 | 8/2005 | Thomenius et al. |
| 7,006,955 B2 * | 2/2006 | Daft et al. ..................... 703/5 |

FOREIGN PATENT DOCUMENTS

| | | |
|---|---|---|
| EP | 1 026 663 A2 | 9/2000 |
| WO | WO 00/05001 | 3/2000 |

OTHER PUBLICATIONS

Dietz et al., Wideband Annular Array Response, 1978 Ultrasonics Symp. Proc., pp. 206-211.

Bailey et al., A Computer-Controlled Transducer for Real-Time Three-Dimensional Imaging, Acoustical Imaging, vol. 18, Editors: Lee and Wade, Plenum Press, New York, 1991, pp. 543-551.

Ergun et al., Fabrication and Characterization of 1-Dimensional and 2-Dimensional CMUT Arrays etc., IEEE, 2002, pp. 2361-2367.

Orallean et al., Capacitive Micromachined Ultrasonic Transducers: Next-Generation Arrays for Acoustic Imaging, IEEE Trans. Ultrasonics, Ferroelectronics and Freq. Control, vol. 29, No. 11, Nov. 2002, pp. 1596-1610.

Jin et al., Micromachined Capacitive Ultrasonic Immersion Transducer for Medical Imaging Proc. 20$^{th}$ Annual Int'l Conf. IEEE Engineering in Medicine and Biology Society, vol. 20, No. 2, 1998, pp. 779-782.

* cited by examiner

INCREASING DELAY

OPTIMIZED SWITCHING CONFIGURATIONS FOR RECONFIGURABLE ARRAYS OF SENSOR ELEMENTS

RELATED PATENT APPLICATION

This application is a continuation-in-part of and claims priority from U.S. patent application Ser. No. 10/383,990 filed on Mar. 6, 2003 now U.S. Pat. No. 6,865,140 and entitled "Mosaic Arrays Using Micromachined Ultrasound Transducers".

STATEMENT REGARDING FEDERALLY SPONSORED RESEARCH AND DEVELOPMENT

The United States Government may have certain rights in this invention pursuant to U.S. Government Contract Number DAMD17-02-1-0181 awarded by the U.S. Army.

BACKGROUND OF THE INVENTION

This invention generally relates to reconfigurable arrays of sensors (e.g., optical, thermal, pressure, ultrasonic). In particular, the invention relates to reconfigurable micromachined ultrasonic transducer (MUT) arrays. One specific application for MUTs is in medical diagnostic ultrasound imaging systems. Another specific example is for non-destructive evaluation (NDE) of materials, such as castings, forgings, or pipelines.

Conventional ultrasound imaging systems comprise an array of ultrasonic transducers that are used to transmit an ultrasound beam and then receive the reflected beam from the object being studied. Such scanning comprises a series of measurements in which the focused ultrasonic wave is transmitted, the system switches to receive mode after a short time interval, and the reflected ultrasonic wave is received, beamformed and processed for display. Typically, transmission and reception are focused in the same direction during each measurement to acquire data from a series of points along an acoustic beam or scan line. The receiver is continuously refocused along the scan line as the reflected ultrasonic waves are received.

For ultrasound imaging, the array typically has a multiplicity of transducers arranged in one or more rows and driven with separate voltages in transmit. By selecting the time delay (or phase) and amplitude of the applied voltages, the individual transducers can be controlled to produce ultrasonic waves that combine to form a net ultrasonic wave that travels along a preferred vector direction and is focused in a selected zone along the beam.

The same principles apply when the transducer probe is employed to receive the reflected sound in a receive mode. The voltages produced at the receiving transducers are summed so that the net signal is indicative of the ultrasound reflected from a single focal zone in the object. As with the transmission mode, this focused reception of the ultrasonic energy is achieved by imparting separate time delay (and/or phase shifts) and gains to the signal from each receiving transducer. The time delays are adjusted with increasing depth of the returned signal to provide dynamic focusing on receive.

The quality or resolution of the image formed is partly a function of the number of transducers that respectively constitute the transmit and receive apertures of the transducer array. Accordingly, to achieve high image quality, a large number of transducers is desirable for both two- and three-dimensional imaging applications. The ultrasound transducers are typically located in a hand-held transducer probe that is connected by a flexible cable to an electronics unit that processes the transducer signals and generates ultrasound images. The transducer probe may carry both ultrasound transmit circuitry and ultrasound receive circuitry.

A reconfigurable ultrasound array is one that allows groups of subelements to be connected together dynamically so that the shape of the resulting element can be made to match the shape of the wave front. This can lead to improved performance and/or reduced channel count. Reconfigurability can be achieved using a switching network.

Little if any work has gone into algorithms for improving the performance of the switching networks required for beamforming. However, switching or multiplexing has been used in several cases for much more limited reconfigurability. Examples of this include: multiplexing with synthetic apertures to increase aperture size, multi-row arrays, and the multiplexing used for scanning in linear arrays. In all these cases the reconfigurability is extremely limited and the need for optimizing the switching network is avoided.

Recently semiconductor processes have been used to manufacture ultrasonic transducers of a type known as micromachined ultrasonic transducers (MUTs), which may be of the capacitive (MUT) or piezoelectric (PMUT) variety. MUTs are tiny diaphragm-like devices with electrodes that convert the sound vibration of a received ultrasound signal into a modulated capacitance. For transmission the capacitive charge is modulated to vibrate the diaphragm of the device and thereby transmit a sound wave. One advantage of MUTs is that they can be made using semiconductor fabrication processes, such as microfabrication processes grouped under the heading "micromachining". The systems resulting from such micromachining processes are typically referred to as "micromachined electro-mechanical systems (MEMS).

The cMUTs are usually hexagonal-shaped structures that have a membrane stretched across them. This membrane is held close to the substrate surface by an applied bias voltage. By applying an oscillatory signal to the already biased cMUT, the membrane can be made to vibrate, thus allowing it to radiate acoustical energy. Likewise, when acoustic waves are incident on the membrane the resulting vibrations can be detected as voltage changes on the cMUT. A cMUT cell is the term used to describe a single one of these hexagonal "drum" structures. The cMUT cells can be very small structures. Typical cell dimensions are 25-50 microns from flat edge to flat edge on the hexagon. The dimensions of the cells are in many ways dictated by the designed acoustical response. It may not be possible to create larger cells that still perform well in terms of frequency response and sensitivity desired.

Unfortunately, it is difficult to produce electronics that would allow individual control over such small cells. While in terms of the acoustical performance of the array as a whole, the small cell size is excellent and leads to great flexibility, control is limited to larger structures. Grouping together multiple cells and connecting them electrically allows one to create a larger subelement, which can have the individual control while maintaining the desired acoustical response. So a subelement is a group of electrically connected cells that cannot be reconfigured. For the purpose of this disclosure, the subelement is the smallest independently controlled acoustical unit. One can form rings or elements by connecting subelements together using a switching network. The elements can be reconfigured by changing the state of the switching network. However, subelements comprise connected cells that are not switchably disconnectable and thus cannot be reconfigured. All of the following analysis is also valid if the array is made of PZT or some other more common or future transducer technology.

Reconfigurability using silicon-based ultrasound transducer subelements was described in U.S. patent application Ser. No. 10/383,990. One form of reconfigurability is the mosaic annular array, also described in that patent application. The mosaic annular array concept involves building annular elements by grouping subelements together using a reconfigurable electronic switching network. The goal is to reduce the number of beamforming channels, while maintaining image quality and improving slice thickness. To reduce system channels, the mosaic annular array makes use of the fact that for an unsteered beam, the delay contours on the surface of the underlying two-dimensional transducer array are circular. In other words, the iso-delay curves are annuli about the center of the beam. The circular symmetry of the delays leads to the obvious grouping of those subelements with common delays and leads to the annular array concept. The reconfigurability can be used to step the beam along the larger underlying two-dimensional transducer array in order to form a scan or image. The reconfigurability might also be used to improve performance for multiple transmit applications by assigning more channels to the smaller active aperture in the near field. There are many other applications where reconfigurability might prove useful.

Reconfigurable ultrasound arrays require a complex switching network that may be difficult or impossible to implement with currently available electronics. There is a need for a simplified switching network that maintains optimum performance by carefully choosing the switching configuration.

BRIEF DESCRIPTION OF THE INVENTION

The invention is directed to reconfigurable arrays of sensors and methods for optimizing the switching configuration for (i.e., maximizing the performance of) such arrays. The sensors may be optical, thermal or pressure sensors or ultrasonic transducers. The embodiment disclosed herein uses a two-dimensional array of capacitive micro-machined ultrasound transducers (cMUTs) as the underlying grid from which larger elements are constructed. The present invention is not limited, however, to cMUT structures and is equally applicable to other conventional or future transducer technologies.

One aspect of the invention is a method for implementing a switching configuration that minimizes the errors introduced by a network of switches during control of a reconfigurable array of sensor elements, comprising the following steps: (a) generating an initial switching configuration; and (b) performing an iterative algorithm comprising the following steps: (i) inputting a switch configuration into a model of the system that calculates the response of the system, taking into account all of the switching network errors, the initial switching configuration being inputted at the start and successively derived modified switching configurations being inputted in succession thereafter; (ii) generating an image or radiation pattern using the model with the inputted switch configuration; (iii) calculating a value for a cost function based at least in part on data representing the generated pattern; (iv) determining whether the calculated value substantially represents a minimum for the cost function; and (v) if the calculated value is not a minimum for the cost function, modifying the current switching configuration as a function of the results of the value calculation to arrive at a modified switching configuration, steps (i) through (v) being repeated for each switching configuration; and (c) if the calculated value is a minimum for the cost function, configuring the switching network with the modified switching configuration that caused the cost function value to be minimized.

Another aspect of the invention is a method for implementing a switching configuration that minimizes the errors introduced by a network of switches during control of a reconfigurable array of sensor elements, comprising the following steps: (a) generating an initial switching configuration; and (b) performing an iterative algorithm comprising the following steps: (i) inputting a switch configuration into a system, the initial switching configuration being inputted at the start and successively derived modified switching configurations being inputted in succession thereafter; (ii) determining the performance of the system with the inputted switch configuration; (iii) calculating a value for a cost function based at least in part on data representing the determined performance of the system; (iv) determining whether the calculated value substantially represents a minimum for the cost function; and (v) if the calculated value is not a minimum for the cost function, modifying the current switching configuration as a function of the results of the value calculation to arrive at a modified switching configuration, steps (i) through (v) being repeated for each switching configuration; and (c) if the calculated value is a minimum for the cost function, configuring the switching network with the modified switching configuration that caused the cost function value to be minimized.

A further aspect of the invention is a method for operating an ultrasound imaging system having an array of ultrasonic transducer elements that are reconfigurable by controlling the respective states of a network of switches, comprising the following steps: (a) optimizing a first switching configuration for use in a first operating state of the ultrasound imaging system; and (b) optimizing a second switching configuration for use in a second operating state of the ultrasound imaging system, wherein the optimizing steps involve minimizing a cost function using an iterative algorithm.

Yet another aspect of the invention is a method for operating an ultrasound imaging system having an array of ultrasonic transducer elements that are reconfigurable by controlling the respective states of a network of switches, comprising the following steps: (a) optimizing a first switching configuration for use in a first operating state of the ultrasound imaging system by minimizing a first cost function using a first iterative algorithm; and (b) optimizing a second switching configuration for use in a second operating state of the ultrasound imaging system by minimizing a second cost function using a second iterative algorithm, the second cost function being different than said first cost function.

A further aspect of the invention is a method for operating an ultrasound imaging system having an array of ultrasonic transducer elements that are reconfigurable by controlling the respective states of a network of switches, comprising the following steps: (a) optimizing a first switching configuration that establishes a first aperture comprising a first set of selected ultrasonic transducer elements; and (b) optimizing a second switching configuration that establishes a second aperture comprising a second set of selected ultrasonic transducer elements, wherein the beam center of the second aperture is stepped by a fraction of an ultrasonic transducer element relative to the beam center of the first aperture.

Other aspects of the invention are disclosed and claimed below.

BRIEF DESCRIPTION OF THE DRAWINGS

Reference will now be made to the drawings in which similar elements in different drawings bear the same reference numerals.

DETAILED DESCRIPTION OF THE INVENTION

The invention is directed to a reconfigurable switching matrix and a method for optimizing switching configurations for such a matrix and its associated array of sensor elements. For the purposes of illustration, the reconfigurable array and the optimization method will be described with reference to capacitive micromachined ultrasonic transducers (cMUTs). However, it should be understood that the aspects of the invention disclosed herein are not limited in their application to probes employing cMUTs, but rather may also be applied to probes that employ pMUTs or even diced piezoceramic arrays where each of the diced subelements are connected by interconnect means to an underlying switching layer. The same aspects of the invention also have application in reconfigurable arrays of optical, thermal or pressure sensors.

Figure 1:
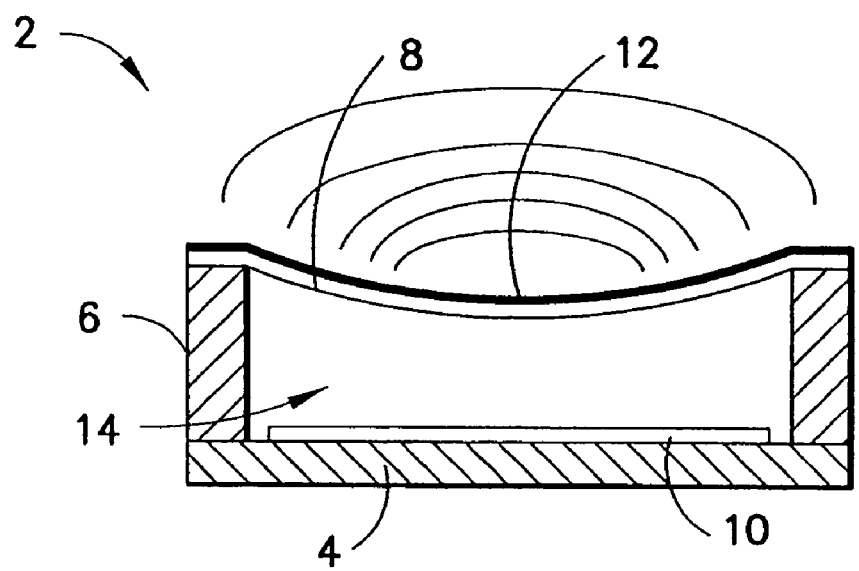
FIG. 1 is a drawing showing a cross-sectional view of a typical cMUT cell.

Referring to FIG. 1, a typical cMUT transducer cell 2 is shown in cross section. An array of such cMUT transducer cells is typically fabricated on a substrate 4, such as a heavily doped silicon (hence, semiconductive) wafer. For each cMUT transducer cell, a thin membrane or diaphragm 8, which may be made of silicon nitride, is suspended above the substrate 4. The membrane 8 is supported on its periphery by an insulating support 6, which may be made of silicon oxide or silicon nitride. The cavity 14 between the membrane 8 and the substrate 4 may be air- or gas-filled or wholly or partially evacuated. Typically, cMUTs are evacuated as completely as the processes allow. A film or layer of conductive material, such as aluminum alloy or other suitable conductive material, forms an electrode 12 on the membrane 8, and another film or layer made of conductive material forms an electrode 10 on the substrate 4. Alternatively, the bottom electrode can be formed by appropriate doping of the semiconductive substrate 4.

The two electrodes 10 and 12, separated by the cavity 14, form a capacitance. When an impinging acoustic signal causes the membrane 8 to vibrate, the variation in the capacitance can be detected using associated electronics (not shown in FIG. 1), thereby transducing the acoustic signal into an electrical signal. Conversely, an AC signal applied to one of the electrodes will modulate the charge on the electrode, which in turn causes a modulation in the capacitive force between the electrodes, the latter causing the diaphragm to move and thereby transmit an acoustic signal.

The individual cells can have round, rectangular, hexagonal, or other peripheral shapes. Hexagonal shapes provide dense packing of the cMUT cells of a transducer subelement. The cMUT cells can have different dimensions so that the transducer subelement will have composite characteristics of the different cell sizes, giving the transducer a broadband characteristic.

Unfortunately, it is difficult to produce electronics that would allow individual control over such small cells. While in terms of the acoustical performance of the array as a whole, the small cell size is excellent and leads to great flexibility, control is limited to larger structures. Grouping together multiple cells and connecting them electrically allows one to create a larger subelement, which can have the individual control while maintaining the desired acoustical response. One can form rings or elements by connecting subelements together using a switching network. The elements can be reconfigured by changing the state of the switching network. However, individual subelements cannot be reconfigured to form different subelements.

MUT cells can be connected together (i.e., without intervening switches) in the micromachining process to form subelements. The term "acoustical subelement" will be used in the following to describe such a cluster. These acoustical subelements will be interconnected by microelectronic switches to form larger elements by placing such switches within the silicon layer or on a different substrate situated directly adjacent to the transducer array.

As used herein, the term "acoustical subelement" is a single cell or a group of electrically connected cells that cannot be reconfigured, i.e., the subelement is the smallest independently controlled acoustical unit. The term "subelement" means an acoustical subelement and its associated integrated electronics. An "element" is formed by connecting subelements together using a switching network. The elements can be reconfigured by changing the state of the switching network. At least some of the switches included in the switching network are part of the "associated integrated electronics", as explained in greater detail below.

Figure 2:
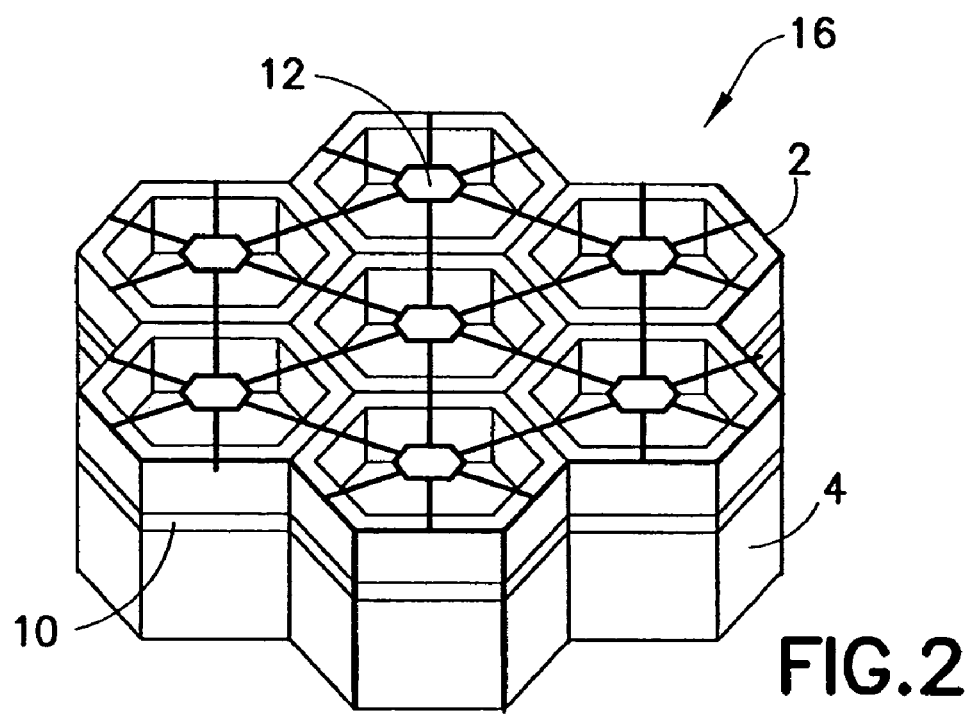
FIG. 2 is a drawing showing a "daisy" subelement formed from seven hexagonal MUT cells having their top and bottom electrodes respectively connected together without intervening switches. This drawing is taken from U.S. patent application Ser. No. 10/383,990.

For the purpose of illustration, FIG. 2 shows a "daisy" transducer subelement 16 made up of seven hexagonal cMUT cells 2: a central cell surrounded by a ring of six cells, each cell in the ring being contiguous with a respective side of the central cell and the adjoining cells in the ring. The top electrodes 12 of each cMUT cell 2 are electrically coupled together by connections that are not switchably disconnectable. In the case of a hexagonal array, six conductors radiate outward from the top electrode 12 and are respectively connected to the top electrodes of the neighboring cMUT cells (except in the case of cells on the periphery, which connect to three, not six, other cells). Similarly, the bottom electrodes 10 of each cell 2 are electrically coupled together by connections that are not switchably disconnectable, forming a seven-times-larger capacitive transducer subelement 16.

Subelements of the type seen in FIG. 2 can be arranged to form a two-dimensional array on a semiconductive (e.g., silicon) substrate. These subelements can be reconfigured to form elements, such as annular rings, using a switching network. Reconfigurability using silicon-based ultrasound transducer subelements was described in U.S. patent application Ser. No. 10/383,990. One form of reconfigurability is the mosaic annular array, also described in that patent application. The mosaic annular array concept involves building annular elements by grouping subelements together using a reconfigurable electronic switching network. The goal is to reduce the number of beamforming channels, while maintaining image quality and improving slice thickness. To reduce system channels, the mosaic annular array makes use of the fact that for an unsteered beam, the delay contours on the surface of the underlying two-dimensional transducer array are circular. In other words, the iso-delay curves are annuli about the center of the beam. The circular symmetry of the delays leads to the obvious grouping of those subelements with common delays. The reconfigurability can be used to step the beam along the larger underlying two-dimensional transducer array in order to form a scan or image.

Figure 3:
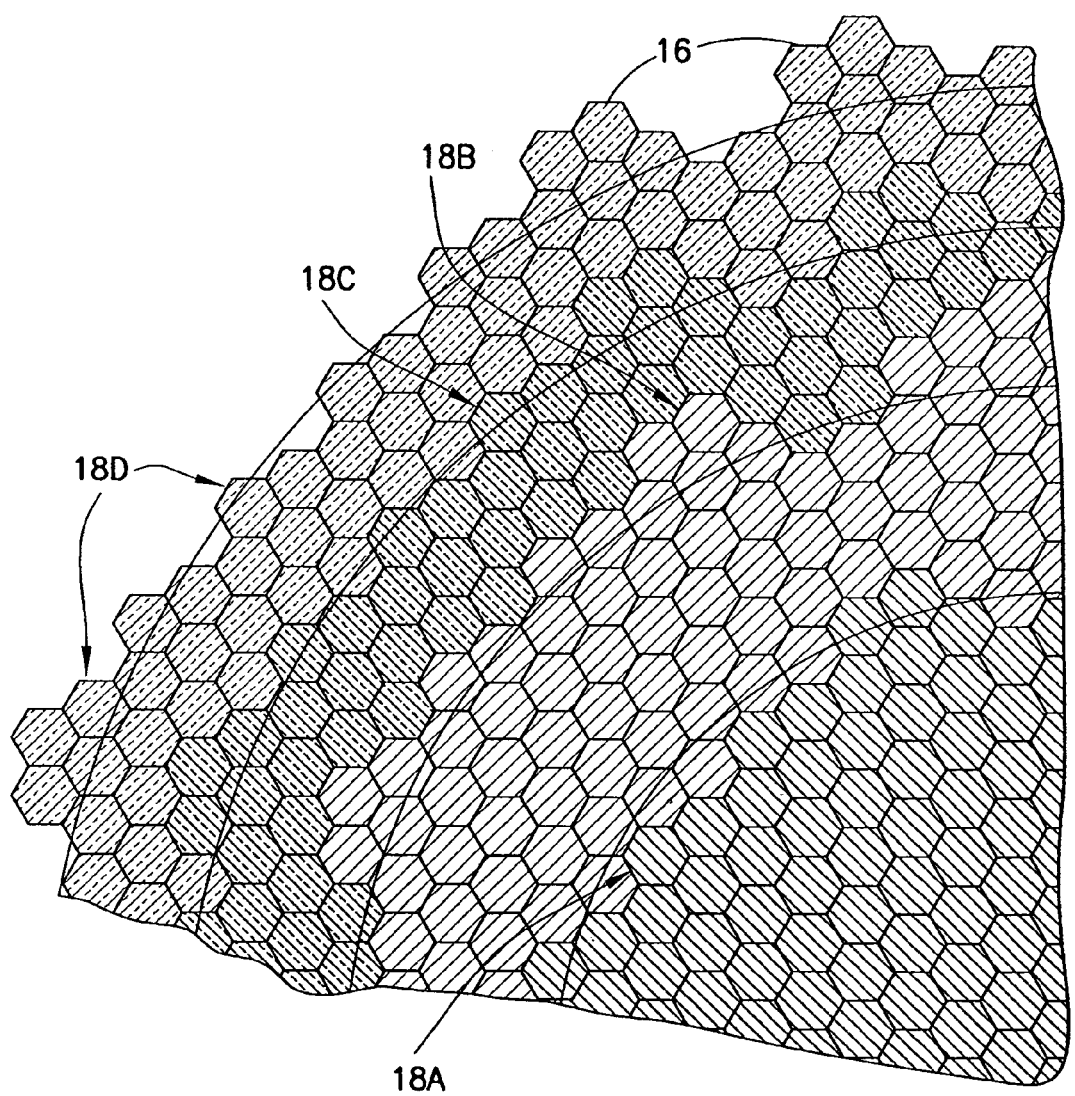
FIG. 3 is a drawing showing a sector of a mosaic array comprising four annular elements as disclosed in U.S. patent application Ser. No. 10/383,990, each element consisting of a tessellation of "daisy" subelements configured to have approximately equal area per element.

There are numerous ways in which one can form transducer arrays using MUT cells and acoustical subelements. FIG. 3 shows one example of tessellations of acoustical subelements to form a mosaic array. In the embodiment shown in FIG. 3, four approximately annular elements (referenced by numerals 18A-D respectively), each comprising a tessellation of "daisy" acoustical subelements (seven MUT cells connected together per subelement), are configured to have approximately equal area per element. The tessellation in each case can be made up of multiple subelement types. The array pattern need not be a tessellation, but can have areas without acoustical subelements. For instance, there could be vias to bring top electrode connections of the acoustical subelement or cells below the array.

The configurations of the invention can be changed to optimize various acoustic parameters such as beamwidth, side lobe level, or depth of focus. Alternatively, the acoustical subelements could be grouped to form one aperture for the transmit operation and immediately switched to another aperture for the receive portion. While FIG. 3 shows respective portions of approximately annular elements, other configurations can be implemented, for example, non-continuous rings, octal rings, or arcs. The choice of pattern will depend on the application needs.

Most apertures will consist of contiguous grouped subelements interconnected to form a single larger element, such as the annular elements shown in FIG. 3. In this case, it is not necessary to connect every subelement directly to its respective bus line. It is sufficient to connect a limited number of subelements within a given group and then connect the remaining subelements to each other. In this way the transmit signal is propagated from the system along the bus lines and into the element along a limited number of access points. From there the signal spreads within the element through local connections.

Given a particular geometry, the reconfigurable array maps acoustical subelements to system channels. This mapping is designed to provide improved performance. The mapping is done through a switching network, which is ideally placed directly in the substrate upon which the cMUT cells are constructed, but can also be in a different substrate integrated adjacent to the transducer substrate. Since cMUT arrays are built directly on top of a silicon substrate, the switching electronics can be incorporated into that substrate. For a PZT or more conventional implementation, the switch network would simply be fabricated in a separate silicon substrate and attached to the PZT array.

Figure 4:
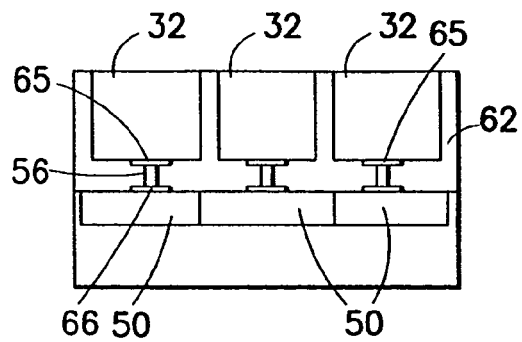
FIG. 4 is a drawing showing a cross-sectional view of a co-integrated cMUT and application specific integrated circuit (ASIC) array.

A cross-sectional view of a co-integrated cMUT and ASIC array is shown in FIG. 4 to illustrate how the connections would be made from the ASIC to the cMUTs. As shown, a single via 56 is used to connect each cMUT subelement 32 to its counterpart CMOS subelement (or "cell") 50. The vias 56, which connect the signal electrodes to respective conductive pads 66 formed on the switch ASIC, may be embedded in an acoustic backing layer 62.

Figure 5:
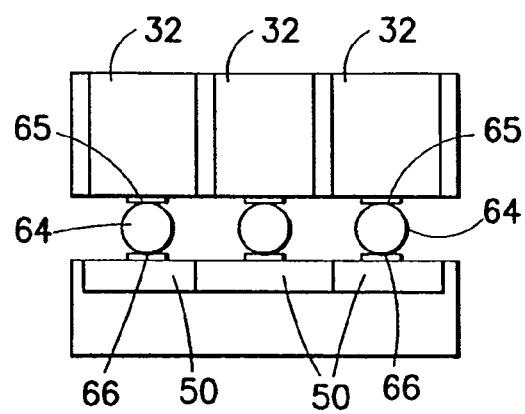
FIG. 5 is a drawing showing a cross-sectional view of a cMUT wafer connected to an ASIC switch matrix.

It is also possible to build the cMUTs on a separate wafer and connect them to the ASIC switch matrix separately, as shown in FIG. 5. Here for example, solder bumps 64 and conductive pads 66 are used to connect the individual cMUT subelements 32 to their switch electronics counterparts 50. Other packaging techniques such as Anisotropic Conductive Film (ACF) or flexible interconnect could also be used.

Figure 6:
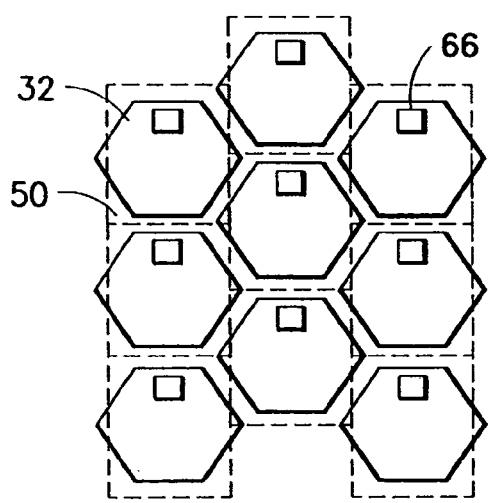
FIG. 6 is a drawing showing a top view of a hexagonal array of cMUT subelements atop a hexagonal array of associated unit switch cells.
Figure 7:
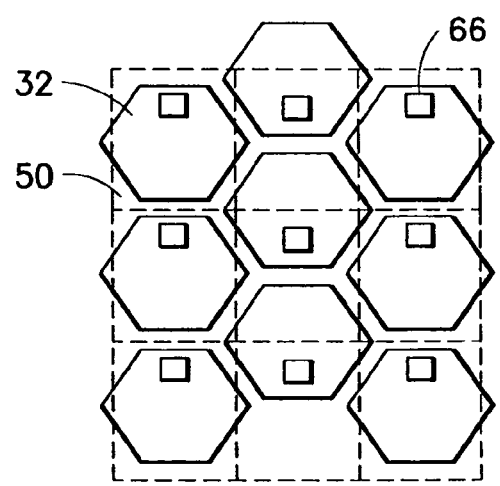
FIG. 7 is a drawing showing a top view of a hexagonal array of cMUT subelements atop a rectangular array of associated unit switch cells.

For optimum packing density it is useful to tile the cMUT subelements 32 and the associated electronics on a hexagonal grid as illustrated in FIG. 6, which shows a top view of the ASIC switch matrix. Here the CMOS unit switch cells 50 are disposed in columns where every second column is offset by half a cell height. With proper choice of the cell dimensions, this will yield a perfect hexagonal array of pads 66 as shown. The vias 56 (also arranged in a hexagonal array) then connect to the respective pads (not shown in FIG. 4) that form the basis of connections to the transducer layer above, comprising a hexagonal array of subelements. A more straightforward ASIC implementation is illustrated in FIG. 7. Here the CMOS unit switch cells 50 are arranged in horizontal rows and vertical columns to form a rectangular grid, while the hexagonal subelements 32 above them form a hexagonal grid. As shown in FIG. 7, the unit switch cell pads 66, arranged in rows and columns to form a rectangular array, still line up correctly to produce the connections such that the unit switch cells 50 are electrically connected to respective hexagonal subelements 32. In either case, the hexagonal grid pattern of the subelements makes it possible to realize the mosaic annular array beam patterns as shown in FIG. 3.

Figure 8:
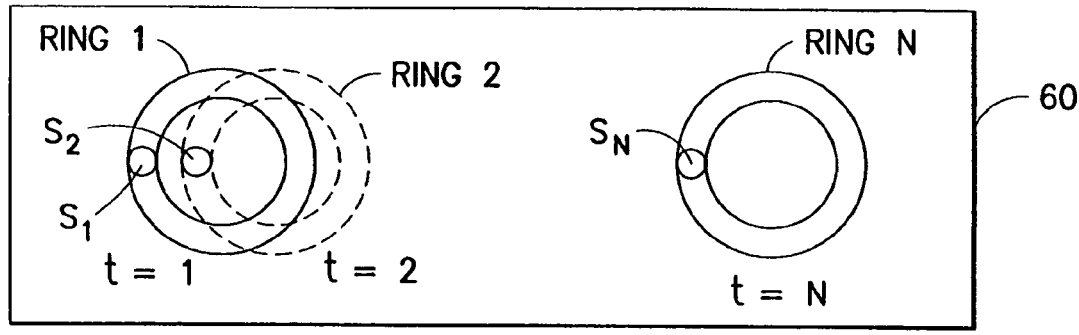
FIG. 8 is a drawing showing translation of an annular transducer element across an array.

In typical operation, the reconfigurable array is programmed with an initial aperture pattern similar to the one shown in FIG. 3. This pattern allows the beamformer to create a beam in front of the array. During imaging, the aperture is scanned across the array 60 as illustrated in FIG. 8, where the ring goes from ring 1 at t=1 to ring 2 at t=2 and finally ring N at t=N, where t is time and N is a positive integer greater than 2. In this way the beam is swept in space in front of the array and the beamformed echoes are used to build up successive lines of the image. The purpose of a reconfigurable array is to be able to accomplish the imaging operation illustrated in FIG. 8 electronically for an arbitrarily complex array pattern. Previous ultrasound scanners are capable of accomplishing electronic scanning but are limited in the complexity of the aperture due to lack of fine distribution of sensor subelements in the elevation direction and fixed geometry.

A fully reconfigurable array as illustrated in FIG. 8 presents a number of significant challenges in implementation. The sensor array is subdivided into tens of thousands of subelements. Beam patterns are built up by grouping the subelements in their connections to a finite number of system transmit/receive and beamforming channels. When used to implement the mosaic annular array concept, the reconfigurable array will form multiple rings that are translated across the array electronically. At each new step in the translation, the entire ring pattern is reprogrammed into the array to create a new configuration. One could also provide the ability to update ring patterns between transmit and receive and at multiple intervals during receive to reduce the distortion of the beam as formed, thereby improving the image quality.

In typical systems, 128 or more beamforming channels are used. Current ultrasound systems use multiplexing architectures that can route the 128 system channels to a fixed number of transducer elements. Using judicious design of these multiplexer networks, it is possible to create a standard scanning pattern with a limited amount of electronics. In most cases however, the scanning pattern is fixed and not reconfigurable due to the limitations of the network. A fully reconfigurable array does not suffer from these limitations; however, it requires a very dense switching matrix to implement it.

As is illustrated in FIG. 8, the fundamental nature of the reconfigurable array requires that any subelement can be arbitrarily connected to any system channel. For example, as the aperture is scanned from the first location to the next location, the subelement S2 first must be part of an internal ring (not shown) and then must be part of ring 2. This means that it must switch from being connected to a first system channel to being connected to a different system channel in a short period of time. This is generally true of a large number of subelements in the array during scanning operation.

Figure 9:
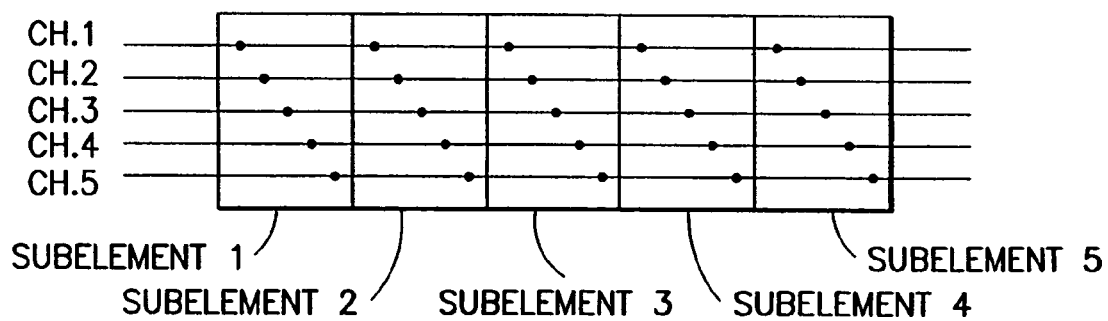
FIG. 9 is a drawing showing an architecture wherein all system channels are distributed throughout the array such that each transducer subelement has access to every system channel.

The simplest way to implement this requirement would be to distribute all system channels throughout the array such that each subelement has access to every system channel. This architecture is illustrated in FIG. 9. Here only five system channels are shown for illustration. Each system channel is bussed through every subelement with local switches used to select which system channel is picked up by which subelement.

In a system where the matrix electronics lie directly behind the transducer array, the space for each subelement's switching electronics is reduced to the size of the subelement. In typical ultrasound systems this size is on the order of a few hundred microns but could be smaller than this. Since the size of a switch varies inversely with its on resistance, one is faced with a tradeoff: more switches with higher on resistance or fewer switches with lower on resistance. Even taking the extreme case however, in which the switches are as small as they can be, it soon becomes apparent that with present semiconductor technologies, many more than 16 switches cannot fit readily in the allotted space. Since for a real array the fully populated architecture of FIG. 9 will contain still more switches, it appears to be intractable with the current state of the art.

Although future technologies may make it quite feasible to integrate many more switches in the same space, progress in ultrasound will tend to reduce the allotted cell size since it is related to the wavelength of the imager, which must shrink for improved image quality. In addition, many more components, such as digital control and transmit/receive circuits, will migrate into this same limited area. Therefore, the fully populated architecture, while attractive for its simplicity, is not immediately tenable or practicable.

Figure 10:
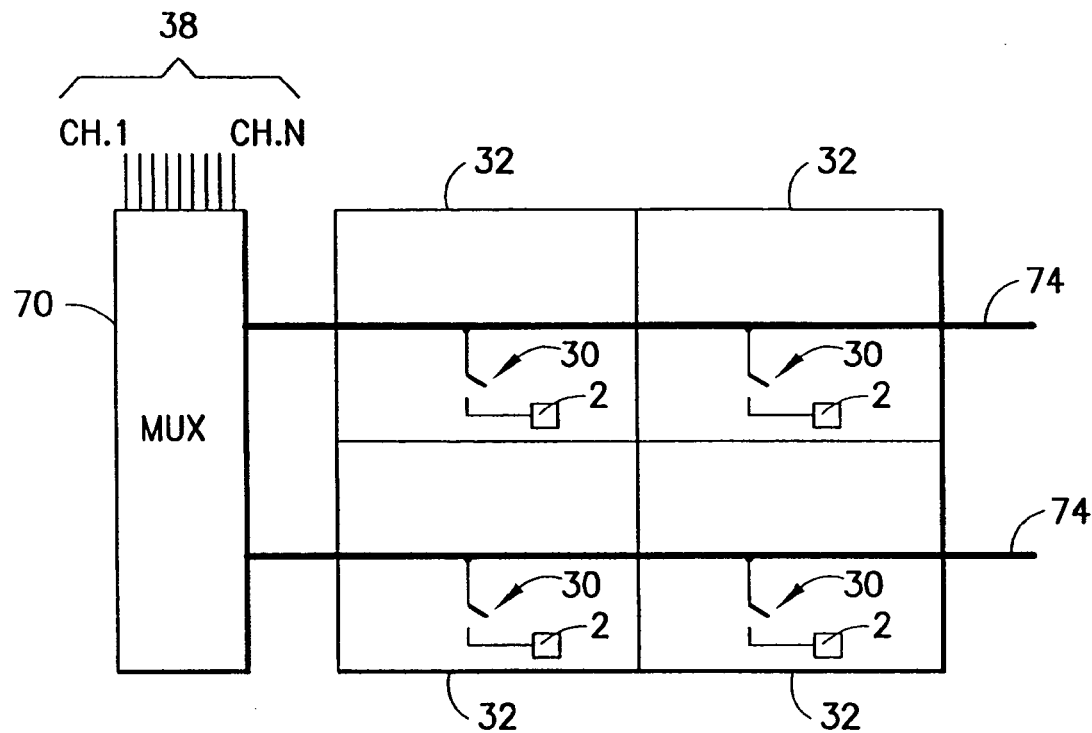
FIG. 10 is a drawing showing an architecture wherein the number of switches in each subelement is limited by having one bus line per row of subelements, the bus lines being connected to system channels via a multiplexer.
Figure 11:
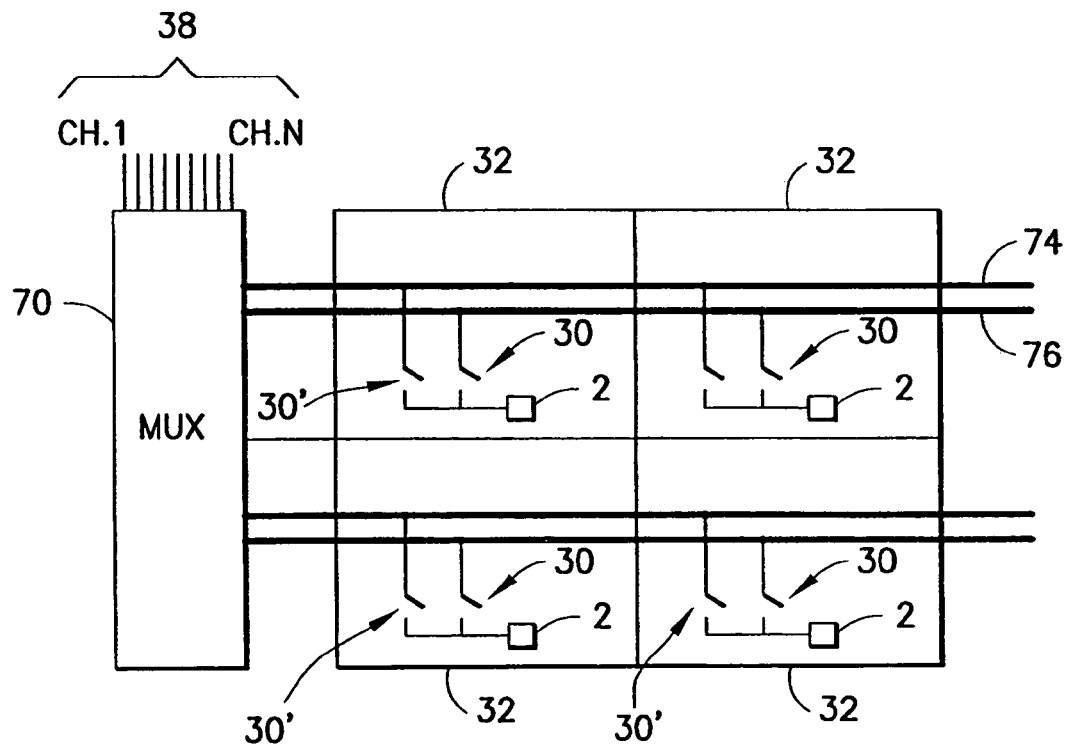
FIG. 11 is a drawing showing an architecture having multiple bus lines per row of subelements, making it possible to group subelements on different system channels within the same row.

A better solution to the interconnect problem described above is to limit the number of switches in each subelement while at the same time providing for the flexibility required in a reconfigurable array. This can be done by using a limited number of bus lines and making these reconfigurable, as is illustrated in FIG. 10. Here a multiplexer 70 is used to arbitrarily select any of the system channels 38 (CH.1 through CH.N) to be connected to any of the bus lines 74, with each row of subelements 32 served by only a single bus line. The cMUT cells 2 of each subelement (only one cMUT cell is shown for each subelement) are connected to a bus line by means of a respective access switch 30. A key feature of this architecture is that many of the switches are located outside of the array and therefore are not constrained by the geometry of the transducers. A one-dimensional pattern can be scanned across the array using this architecture by successively selecting which row of subelements is connected to which system channel. A further improvement to this architecture is shown in FIG. 11. Here multiple bus lines 74, 76 are routed down each row of subelements 32. The cMUT cells 2 of each subelement 32 can be connected to either bus line 74 via access switch 30' or bus line 76 via access switch 30. This architecture provides flexibility in the horizontal direction since it is now possible to group elements on different system channels within the same row.

Figure 12:
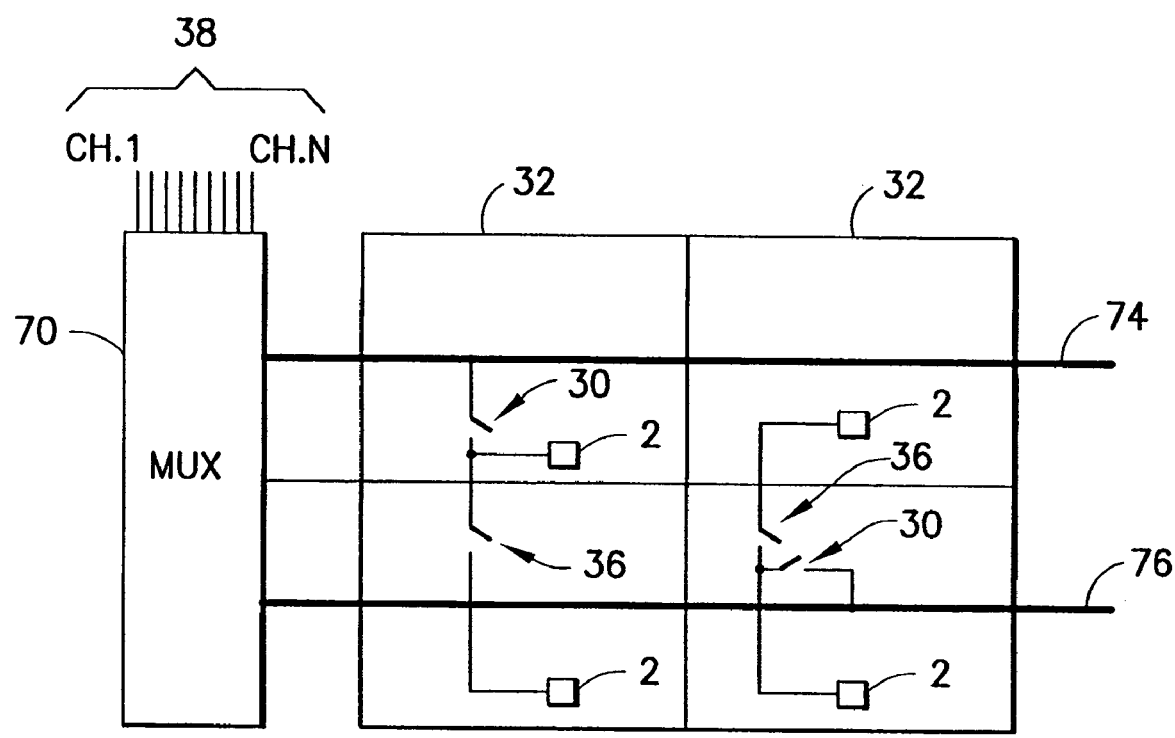
FIG. 12 is a drawing showing an architecture in accordance with one embodiment of the invention that allows a subelement in a first row to connect to a bus line for a second row of subelements by connecting to an access switch of an adjacent subelement in the second row via a matrix switch of the subelement in the first row.

A further improvement to the above architecture can be made by realizing that most apertures will consist of contiguous grouped subelements interconnected to form a single larger element. In this case, it is not necessary to connect every subelement directly to its respective bus line. It is sufficient to connect a limited number of subelements within a given group and then connect the remaining subelements to each other. In this way the transmit signal is propagated from the system along the bus lines and into the element along a limited number of access points. From there the signal spreads within the element through local connections. This architecture is illustrated in FIG. 12. Here individual subelements 32 are able to connect to the bus line associated with their row by way of access switches 30 and are able to connect to the bus line associated with an adjacent row by way of matrix switches 36, which connect one subelement to an adjacent subelement.

Figure 13:
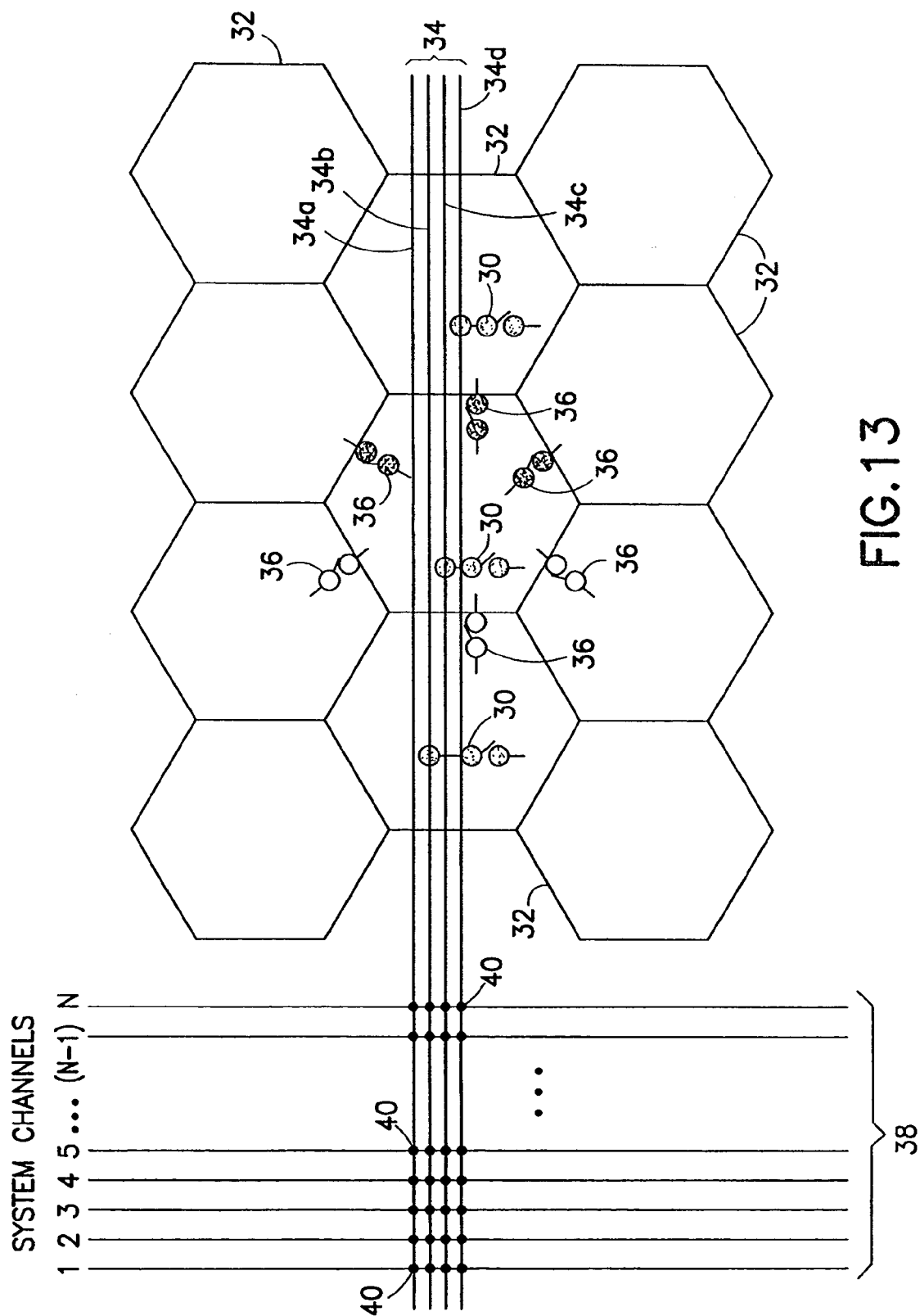
FIG. 13 is a drawing showing an architecture in accordance with another embodiment of the invention that allows a particular subelement in a particular row of a cMUT array to be connected to any one of a multiplicity of system channel bus lines.

One embodiment of the invention, shown in FIG. 13, incorporates all of the above-mentioned improvements together. Here an access switch 30 is used to connect a given subelement 32 to a row bus line of bus 34. This architecture is directly applicable to a mosaic annular array. In such a device multiple rings can be formed using the present architecture, wherein each ring is connected to a single system channel using one or more access switches, each of which is connected to a bus line, which is in turn connected to a system channel.

The access switches are staggered as shown in FIG. 13 to reduce the number required for a given number of bus lines, as discussed further below. Random ordering of access switches to bus lines (not shown) could also be employed to reduce artifacts due to the repeating patterns. More than one access switch in each subelement could be used to improve the flexibility of the array. In such an architecture, a tradeoff between flexibility and number of access switches per subelement would be made where the number is still significantly fewer than the number of bus lines and system channels. It is also possible to use more than one access switch per bus line in each element. This would improve the yield of the device since non-functioning access switches could be bypassed using the redundant access switches.

The row bus lines are connected to the system channels using a cross-point switching matrix as shown in FIG. 13. A sparse cross-point switch could be used as well in which fewer multiplexer switches would be required. Such an architecture would be more efficient in use of space but would require judicious choice of switch configurations to ensure that all bus lines could be properly connected. As shown in FIG. 12, multiple bus lines can be used per row. More bus lines improves flexibility of the array at the expense of more multiplexer switches and more routing area inside the array. It is possible to skip rows or to use different numbers of bus lines on different rows. For example, to conserve area it might be advantageous to share a group of bus lines between every pair of adjacent rows of subelements.

Figure 14:
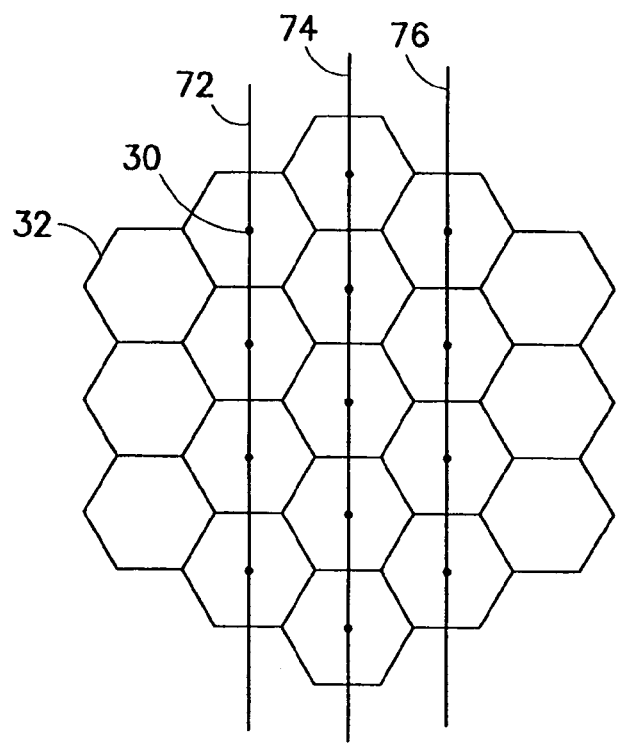
FIG. 14 is a drawing showing a hexagonal array of subelements with bus lines connected to respective columns of subelements via access switches (indicated by solid dots).
Figure 15:
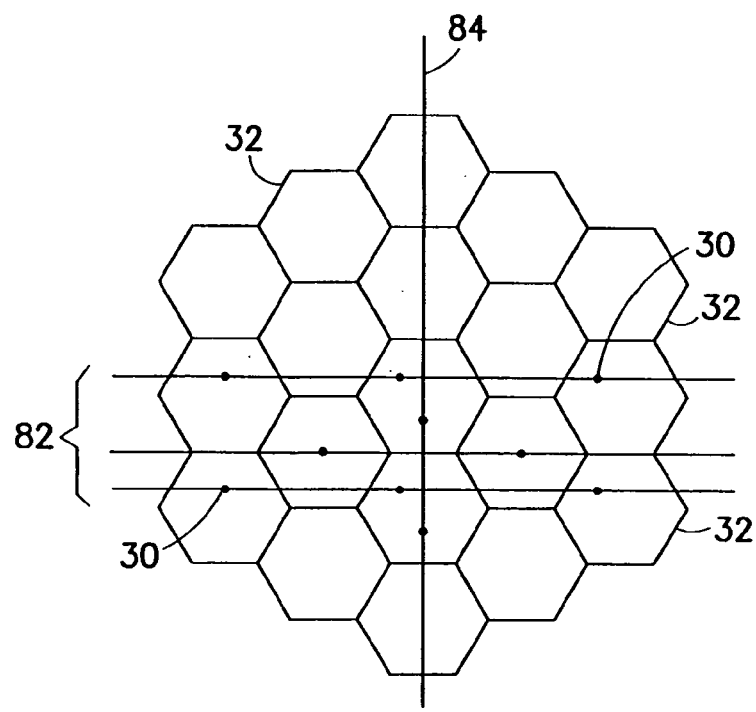
FIG. 15 is a drawing showing a hexagonal array of subelements with some subelements connected to vertical and horizontal bus lines via respective access switches (indicated by solid dots).
Figure 16:
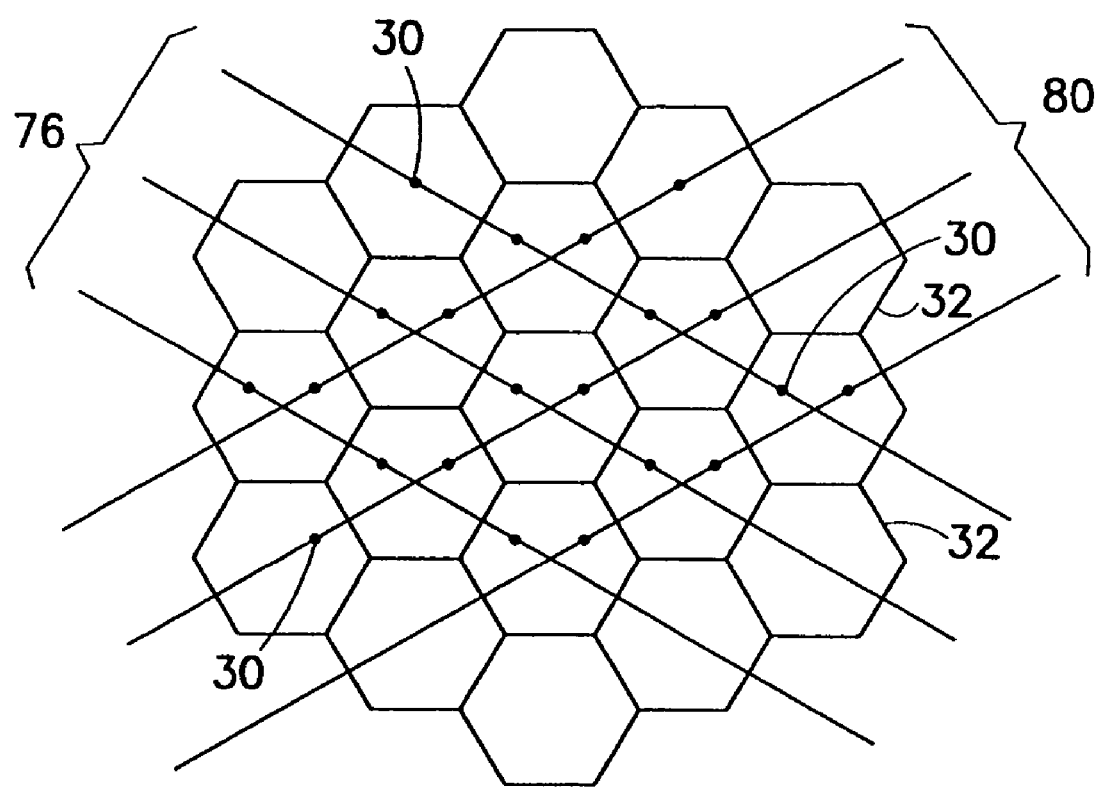
FIG. 16 is a drawing showing a hexagonal array of subelements with bus lines disposed diagonally along the natural axes of the hexagonal array. Access switches are indicated by solid dots.

Although only horizontal bus lines have been discussed thus far, it is also possible to dispose both vertically and horizontally running bus lines within an array. Bus lines could be disposed vertically as illustrated in FIG. 14 (see bus lines 72, 74, 76). Referring to FIG. 15, one set of bus lines 82 could be disposed horizontally and another set 84 disposed vertically. In this case each subelement or group of subelements will be connectable to a vertical bus line via one access switch and will further be connectable to a horizontal bus line via a different access switch. However, in the case where bus lines are run in both directions because the electronic real estate available for bus lines is running low and more bus lines are needed, but there is still only a single access switch in a subelement, then each subelement's access switch could be connected to either the horizontal bus line or the vertical bus line and not both. Finally, bus lines could also be disposed diagonally as illustrated in FIG. 16. These lines 76, 80 respectively run along two of the natural axes of the hexagonal array and would therefore simplify addressing of subelements.

The number of access switches and row bus lines is determined by the size constraints and the application. For the purpose of disclosing one exemplary non-limiting implementation (shown in FIG. 13), a single access switch 30 for each subelement 32 and four row bus lines 34a-34d for each row of the array will be assumed. The second type of switch is a matrix switch 36, which is used to connect a connection point 42 of one subelement (see FIG. 17) to the connection point of a neighboring subelement. This allows an acoustical subelement to be connected to a system channel through the integrated electronics associated with a neighboring acoustical subelement. This also means that an acoustical subelement may be connected to a system channel even though it is not directly connected via an access switch. While FIG. 13 shows three matrix switches per subelement, it is also possible to have fewer than three to conserve area or to allow for switches which have lower on resistance and therefore have larger area. In addition, matrix switches can be used to route around a known bad subelement for a given array. Finally, while hexagonal subelements are shown, rectangular subelements are also possible.

Figure 17:
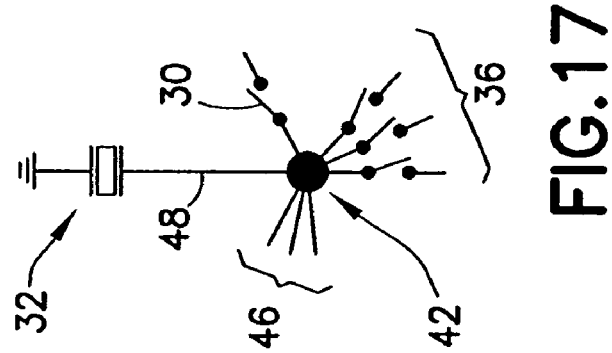
FIG. 17 is a drawing showing connections to a common connection point in the electronics associated with a particular acoustical subelement in accordance with the embodiment depicted in FIG. 13.

Referring to FIG. 17, each of the subelements is connected to a common connection point 42 in the electronics associated with the acoustical subelement 32. This common connection point 42 electrically connects eight components in each subelement. The common connection point 42 connects the acoustic subelement or transducer 32 to the access switch 30 for that subelement, to the three matrix switches 36 associated with that subelement, and to the three matrix switches associated with three neighboring subelements via connections 46. A signal that travels through a matrix switch gets connected to the common connection point of the neighboring subelement.

FIG. 13 depicts how the switching network might work for a particular subelement. This is only an exemplary arrangement. A bus 34, which contains four row bus lines 34a through 34d, runs down the row of subelements 32. FIG. 13 shows only three subelements in this row, but it should be understood that other subelements in this row are not shown. The row bus lines of bus 34 are multiplexed to system channel bus lines of system channel bus 38 at the end of a row by means of multiplexing switches 40, which form a cross-point switching matrix. As seen in FIG. 13, each row bus line 34a-34d can be connected to any one of the system channel bus lines of bus 38 by turning on the appropriate multiplexing switch 40 and turning off the multiplexing switches that connect the particular row bus line to the other system channel bus lines. These multiplexing electronics can be off to the side and thus are not as restricted by size. FIG. 13 shows a fully populated cross-point switch. However, in cases wherein it is not necessary to have switches that allow every bus line to be connected to every system channel, a sparse cross-point switch can be used in which only a small subset of the system channels can be connected to a given bus line, in which case only some of switches 40 depicted in FIG. 13 would be present.

An access switch is so named because it gives a subelement direct access to a bus line. In the exemplary implementation depicted in FIG. 13, there are six other switch connections for each subelement. These connections take the form of matrix switches 36. A matrix switch allows a subelement to be connected to a neighboring subelement. While there are six connections to neighboring subelements for each subelement in this hexagonal pattern, only three switches reside in each subelement while the other three connections are controlled by switches in the neighboring subelements. Thus there is a total of four switches and associated digital logic in each subelement. This is just one exemplary implementation. The number of bus lines, the number of access switches, and the number and topology of the matrix switches could all be different, but the general concept would remain.

Although the access and matrix switches can be separately packaged components, it is possible to fabricate the switches within the same semiconductor substrate on which the MUT array is to be fabricated. These switches may comprise high-voltage switching circuits of the type disclosed in U.S. patent application Ser. No. 10/248,968 entitled "Integrated High-Voltage Switching Circuit for Ultrasound Transducer Array". Each switch comprises two DMOS FETs that are connected back to back (source nodes shorted together) to allow for bipolar operation. Current flows through the switch terminals whenever both FETs are turned on. The states of the switches are controlled by respective switch control circuits. The states of the switch control circuits are in turn dictated by outputs from a programming circuit, which programs the switch control circuits in accordance with an optimized switching configuration derived using the algorithm disclosed herein. A scan controller loads the optimized switching configuration into the programming circuit. Although use of CMOS high-voltage switches is one preferred embodiment, the invention described here is directly applicable to other switching technologies such as low voltage switches, MEMS switches and other future switch technologies in development.

Figure 18:
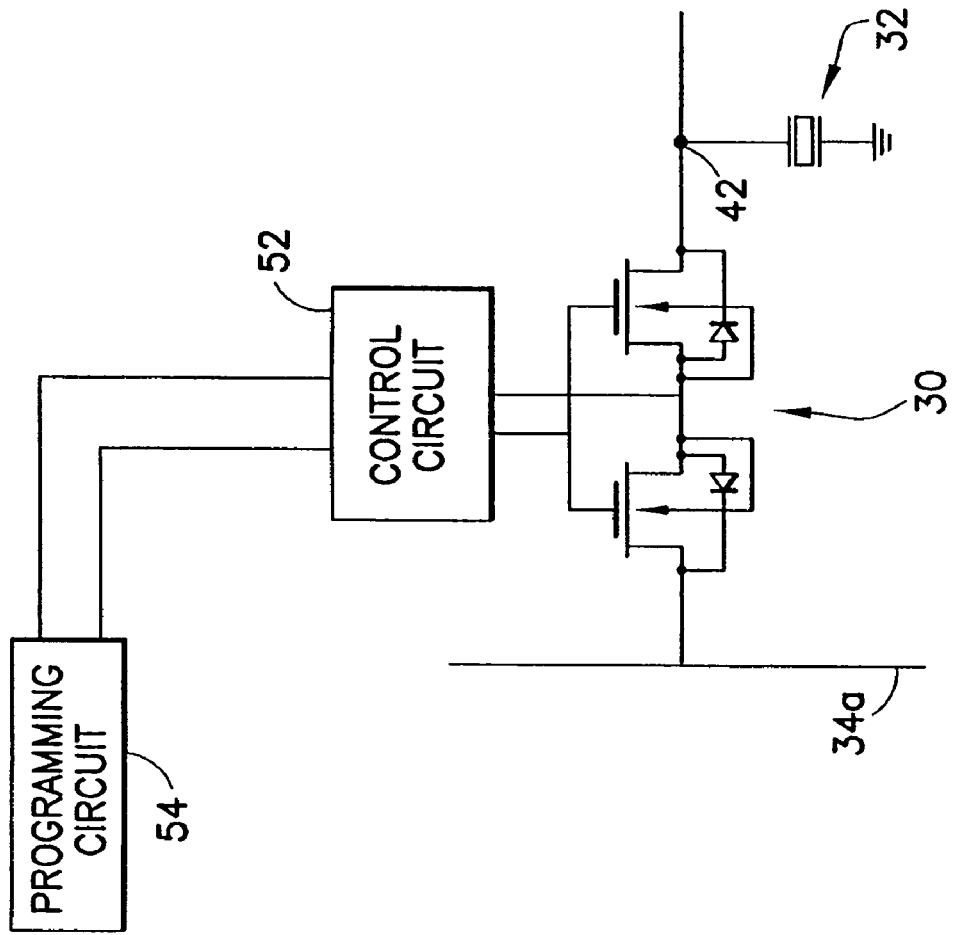
FIG. 18 is a drawing showing an access switch and circuitry for controlling the state of that access switch, as previously disclosed in U.S. patent application Ser. No. 10/248,968.

FIG. 18 shows an acoustical subelement 32 connected to an access switch 30 via a common connection point 42. The six other lines that connect to the connection point 42 are not shown. For this example, the access switch 30 comprises the aforementioned pair of back-to-back DMOS FETs. The control circuit 52 turns the switch 30 on or off as a function of control signals sent by the programming circuit 54. When access switch 30 is turned on, the acoustical subelement 32 (i.e., a subarray of interconnected cMUT cells) is connected to the row bus line 34a. For this configuration, the electronics associated with each acoustical subelement will comprise one access switch, three matrix switches, a respective control circuit for each of these four switches, and a respective conductor connecting the common connection point to the matrix switches of three neighboring subelements (not shown).

The signal that travels from the subelement to the row bus line is the electrical receive signal. Here the receive signal is the electrical response generated by the acoustical subelement when a sound pressure wave interacts with the transducer. The transmit signal, in which an electrical pulse is generated by the ultrasound system, travels from the row bus line to the matrix switch. For a given channel, this electrical excitation pulse travels through a system channel bus line to a row bus line. The signal travels from the row bus line to the acoustical subelement through an access switch and also travels to other subelements through the matrix switches.

The number of switches that fit behind an acoustical subelement is limited. The size of the switch determines the on resistance of the switch and the smaller the switch the larger the on resistance. The delay and distortion caused by the switching increases as the switch on resistance increases. This means that there is a tradeoff between the number of switches behind an acoustical subelement and the delay introduced by those switches. One solution to that tradeoff involves reducing the number of switches to a small number while retaining as much flexibility as possible. This reduction is achieved by using matrix switches to allow acoustic subelements to be attached to a system channel through other subelements, and by limiting the number of access switches to a small number.

The bus lines that connect the access switches to the system channels also take space in the electronics layer, so minimizing the number of bus lines is also beneficial. The number of unique channels that can be directly connected to acoustic subelements in the same row is determined by the number of bus lines. However, since the matrix switches allow subelements in one row to connect to subelements in other rows, the number of channels in a row is increased by the matrix switches. This allows the number of bus lines to be kept small, while still servicing a large number of channels. Of course, having more bus lines increases the flexibility but requires more space.

The use of matrix switches means that the number of access switches behind each subelement can be reduced. In the extreme case there is only one access switch for each subelement. However, if there is more than one bus line, a determination must be made as to which bus line each access switch should be connected. One solution is to stagger the connections so that the bus line connected to repeats every N subelements in a row, where N is a number determined by the requirement of minimum signal distortion as discussed below. Referring to FIG. 13, each subelement 32 in the row is connected to one of the row bus lines in the row bus 34 via a respective access switch 30. This pattern of staggered connections repeats every four subelements. The staggering allows more bus lines with fewer access switches and combined with the matrix switches, still allows for great flexibility as to which system channels can be connected to each subelement. Of course having more than one access switch per cell increases the flexibility of the connections but requires smaller switches with higher on resistance.

Figure 19:
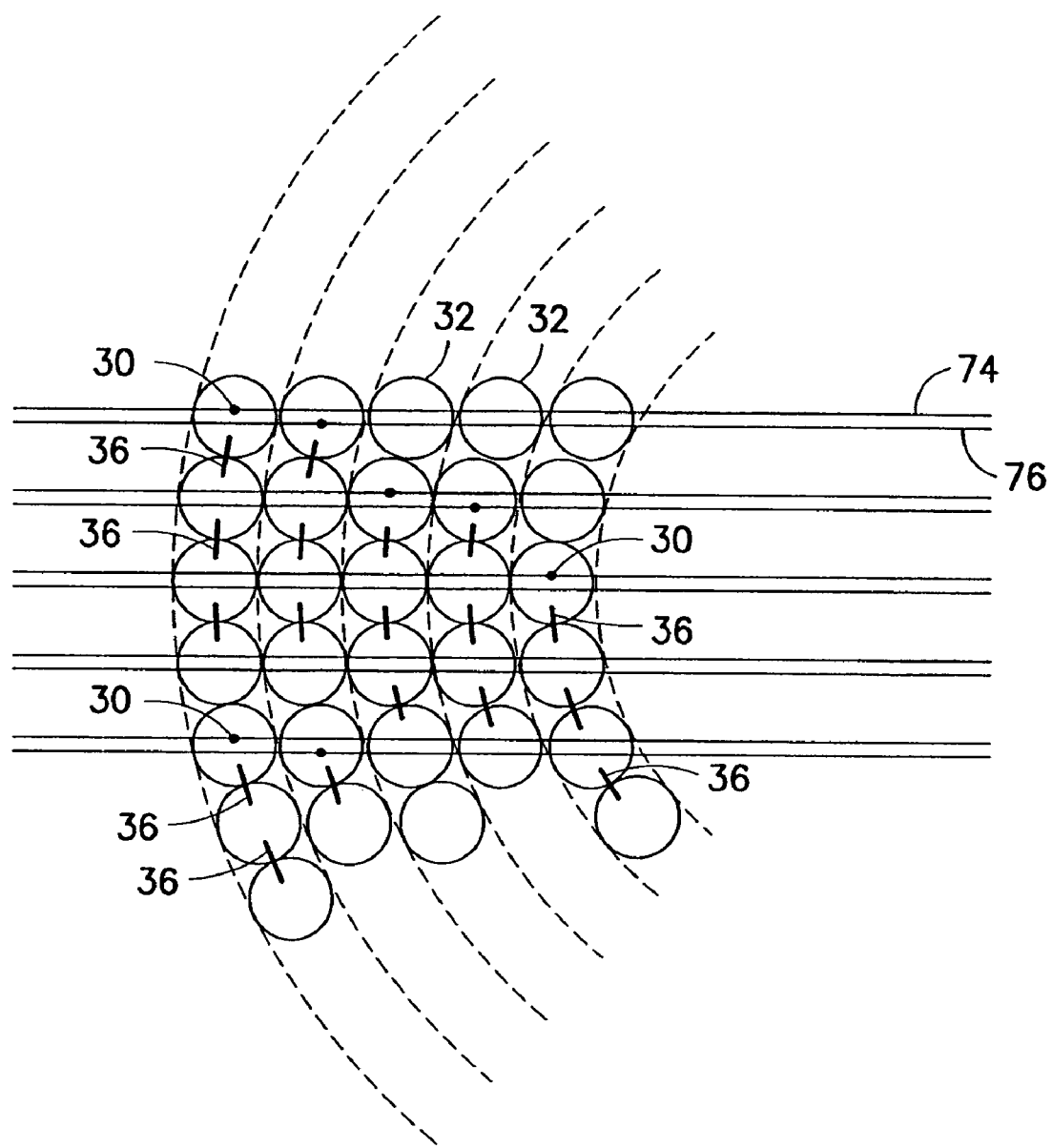
FIG. 19 is a drawing showing an arrangement of access and matrix switches for use with rings (portions of which are indicated by dashed arcs) with single subelement width are packed close together. Access switches are indicated by solid dots; matrix switches are indicated by dashes.

Generally, the number of rows N after which the pattern repeats is determined by the maximum number of matrix switches which can be strung together while still maintaining adequate signal integrity. This number comes out of the understanding that the matrix switch resistance and cMUT capacitances together form an RC delay line with a time constant of delay which varies exponentially with the number of series taps N. This concept is discussed further below. Staggering the access switches on multiple row bus lines allows the number of elements that can be supported to be increased given the constraint of the delay line. As illustrated in FIG. 19, the worst case for the design occurs where rings (portions of which are indicated by dashed arcs) with single subelement width are packed close together. The vertical sections of the ring provide the worst case since bus lines 74, 76 in this design run horizontally. In the horizontal sections of the rings, one could just use a single access switch at every subelement since they would all be the same as the bus lines run parallel to the rings. In the vertical sections however, every row of subelements 32 is associated with a different bus line that is connected to a different system channel. Therefore, subelements spaced vertically in this area can only be supported using matrix switches 36, represented by dashes. In FIG. 19, there are two bus lines per row, and the pattern of access switches 30 (represented by dots) repeats every four rows. At each row, two rings are supported by the two access switches and their associated string of subelements grouped with matrix switches. Since the pattern repeats after four rows, this particular architecture will support a maximum of 2×4=8 rings. In general for an array with M bus lines on each row and N taps for each string of subelements, a maximum of K system channels can be supported where K=M×N. Of course, most sections of the rings will be neither perfectly horizontal nor perfectly vertical. Therefore the task of the system designer is to optimize the array configuration at all points in the aperture under the constraints of the architecture.

Given a particular desired mapping between subelements and system channels, the goal is to determine the optimal switching network configuration that provides or nearly provides that mapping. There may not be a configuration that exactly matches the desired mapping. This depends on the flexibility of the given design, which is controlled by the number of bus lines and the number of access switches. In the case were the desired mapping cannot be created, a close approximation must be chosen. For the mosaic annular version of reconfigurability, the more likely situation is that there will be multiple configurations that provide the desired subelement-to-channel mapping. There might also be multiple approximate configurations for the case in which the desired mapping cannot be exactly created. In these cases, where multiple configurations provide the same subelement-to-system channel mapping, one configuration may be more desirable than another in terms of delay and amplitude performance. One aspect of the invention presented here involves the use of optimization procedures to improve the performance of the imaging system by choosing a configuration with better performance.

The connections between a system channel and a given subelement may be complicated. A switching network configuration defines a complex web of connections among subelements and system channels. The result is that there is not a simple connection from a subelement to a system channel, but rather a connection through a series of switches (both access and matrix) that form a complex delay line structure. On transmit, the signals connected to the same system channel should see the same transmit pulse synchronously. However, in reality the network of switches delays the signals and changes the amplitude and shape of the pulse at each subelement, which sees a different path to the system transmitter.

Figure 20:
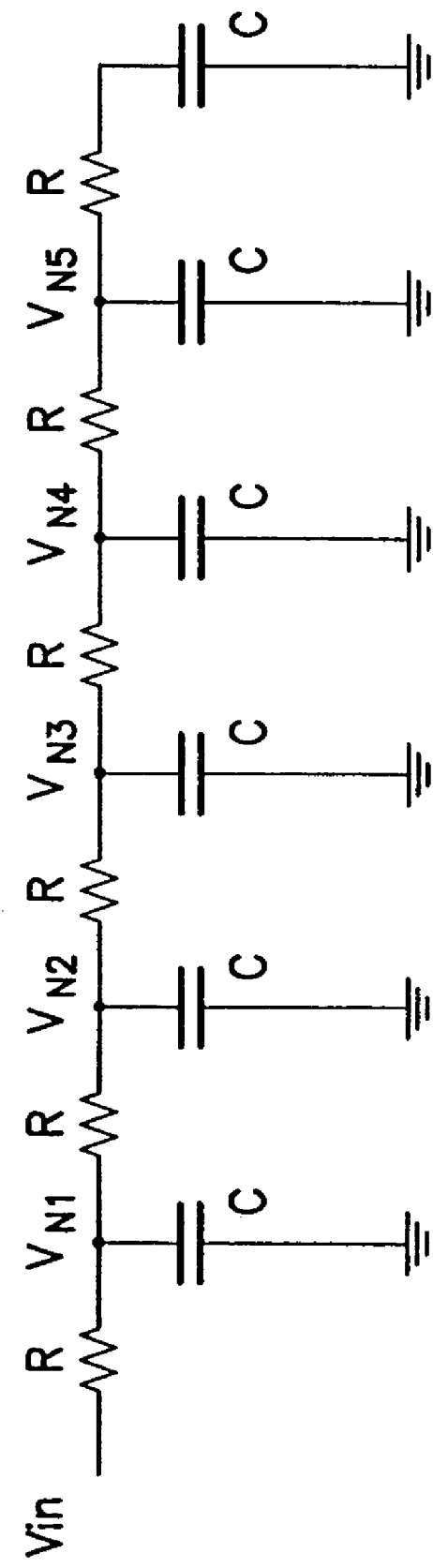
FIG. 20 is a circuit diagram representing a distributed RC delay line.
Figure 21:
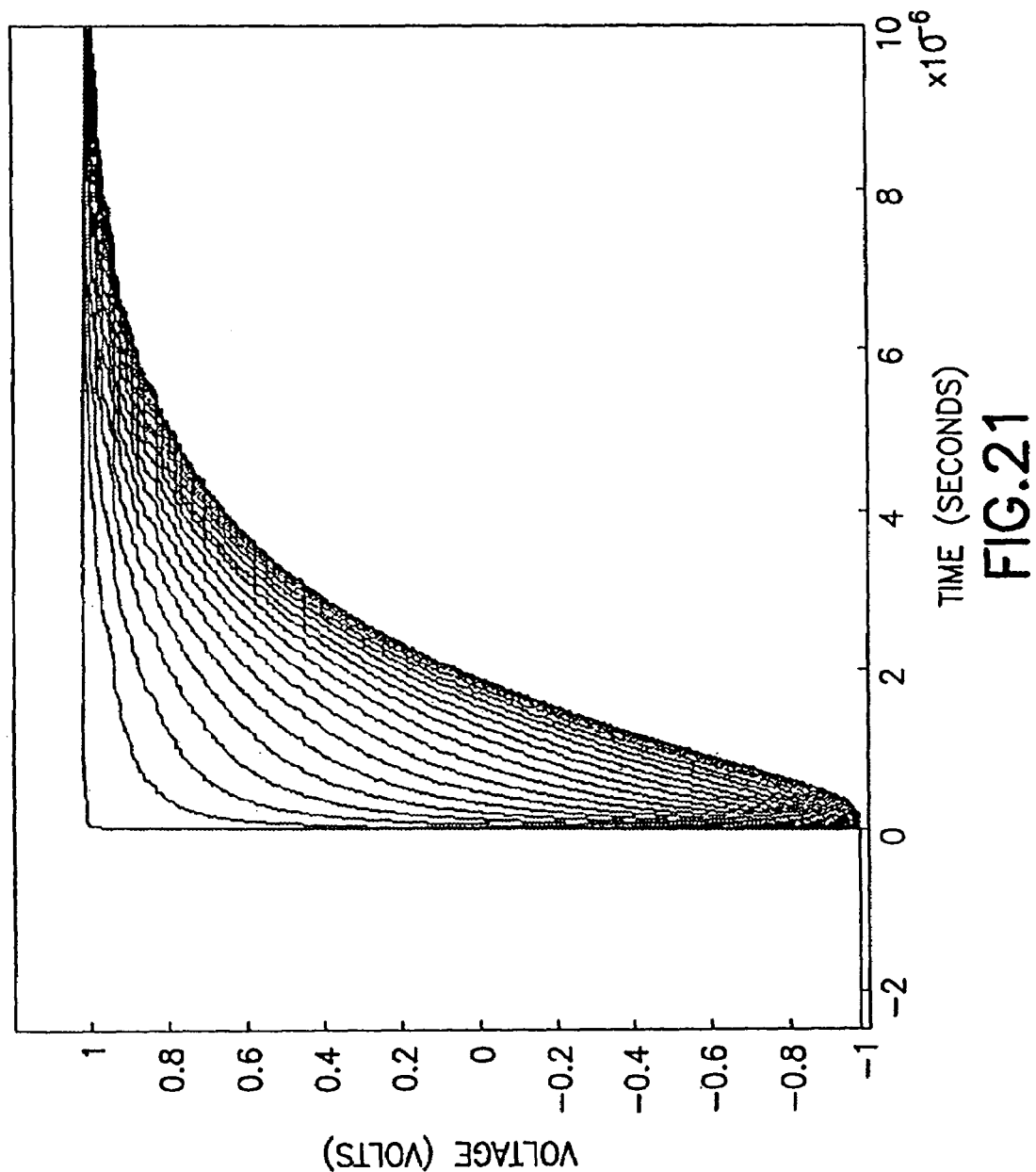
FIG. 21 is a graph of measured delay data for a 20-tap RC delay line.

Simple simulations of delay lines can be used to get an idea of how much delay will be present and how the pulses will be distorted. The transducer array and its associated switch matrix can be modeled as a distributed network of resistances and capacitances. Signals propagate through this network with a delay time that is related to the unit resistance and capacitance of the network. A simple example of such a network is a one-dimensional RC delay line as shown in FIG. 20. In this network, signals propagating from the input incur a delay that is a function of the resistance R and capacitance C as shown. At each node or tap in the network the waveform is shaped differently because it has incurred a different amount of delay relative to the input signal. The worst case delay in a finite RC delay line can be shown to vary with $RCN^2/2$, where N is the number of taps in the delay line. FIG. 21 shows measured data for a 20-tap RC delay line similar to the network shown in FIG. 20. The graph shows a family of curves measured at each tap of the delay line with tap number increasing from left to right. This graph clearly shows the distortion in the voltage waveforms as they propagate through the network. The worst-case delay (defined as the time from step input to midpoint of the output) is seen to be approximated by $RCN^2/2$, which in this experiment is about 25 microseconds. Therefore, a good rule of thumb for design of a reconfigurable ultrasound array is to design the transducer capacitance and switch on resistance such that $RCN^2/2$ is always less than the worst-case delay that can be tolerated in the system. In this case, the number of taps (or switches) N that are tolerated in any given path is limited by the system imaging requirements and the RC time constant of the network.

Figure 22:
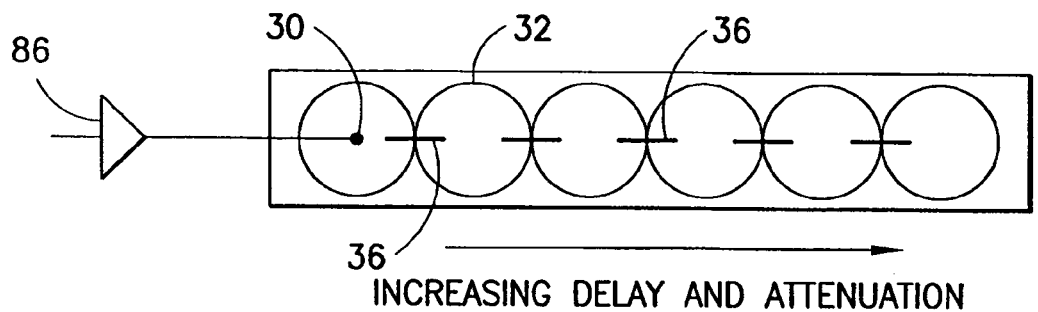
FIG. 22 is a drawing showing a row of subelements connected in series by matrix switches, with the subelement at one end of the row being connected to a bus line by an access switch.

The results discussed above demonstrate that the delay at a particular subelement depends on how many switches the signal must pass through, how many paths the signal has to travel, and how the multiple connections are distributed. Depending on the particular aperture used we can expect to see different delay patterns. Additionally, through simulation and successive approximation one may arrive at improved placement of access switches for a reduced delay. FIG. 22 illustrates how the delay varies with element topology. Item 86 in this example represents a driver, while the remainder of the figure depicts a row of subelements 32 connected in series (to form a linear element) by respective matrix switches 36. The first subelement in the row is connected to the driver 86. To first order, propagation of signals in a delay line can be thought of as diffusion of heat from point heat sources. Keeping in mind this analogy, FIG. 22 shows that delay and attenuation increase in two dimensions as the distance from the forcing nodes or access switches 30 increases.

Figure 23:
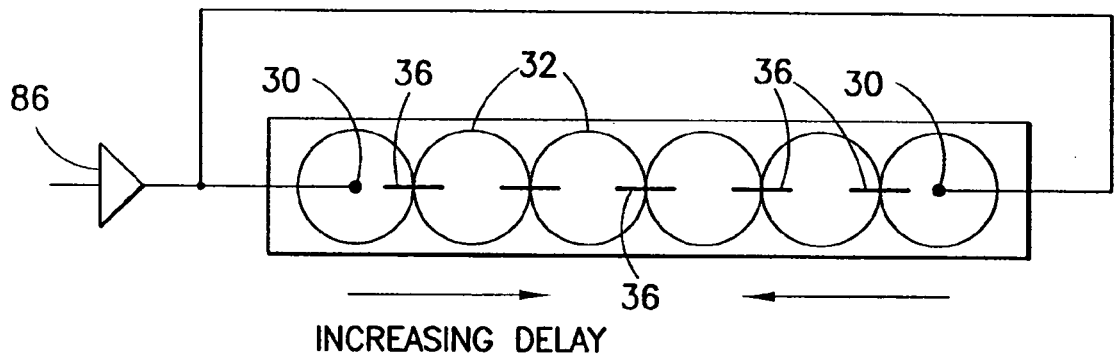
FIG. 23 is a drawing showing a row of subelements with the subelements at the ends of the row being connected to a bus line by respective access switches, and the remaining subelements being connected via matrix switches to one or the other access switch.
Figure 24:
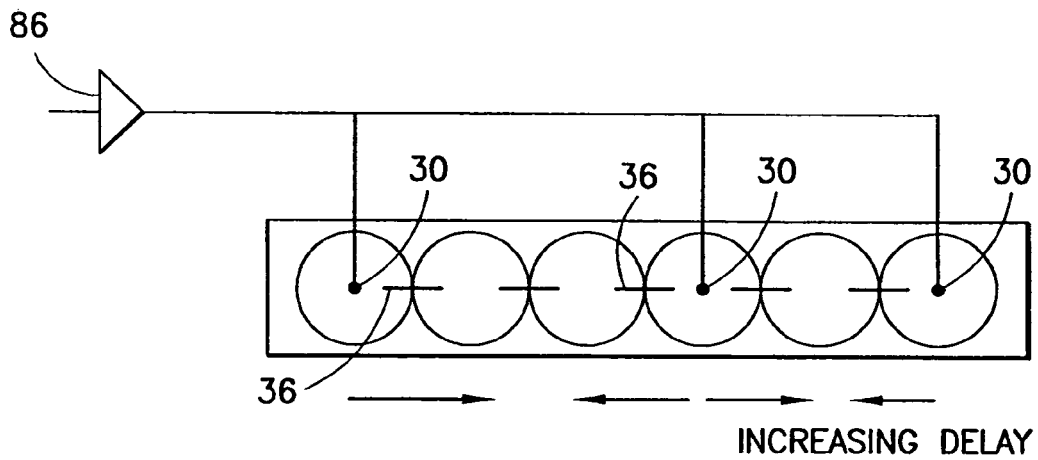
FIG. 24 is a drawing showing a row of subelements with the subelements at the ends of the row and one subelement near the middle of the row being connected to a bus line by respective access switches, and the remaining subelements being connected via matrix switches to a respective access switch.

It is apparent that to reduce signal distortion for every subelement in the aperture, it is best to distribute access switches as uniformly as possible and as densely as possible. Specifically, switches can be configured to ensure that there is a respective different access switch 30 connected at both ends of a long run of matrix switch connections as shown in FIG. 23. With a linear element as shown, significant improvement can be made by placing access switches 30 on both ends of the linear element, especially if the all the subelements are connected together by matrix switches along the linear element such that a continuous path from one end of the linear element to the other exists. The improvement made by connecting both ends of the continuously connected linear element is greater than the improvement the would be made by dividing the same element into two shorter elements, each with their own access switch connection. Still more improvement occurs when the access switches 30 are distributed within the element, as shown in FIG. 24.

Figure 25:
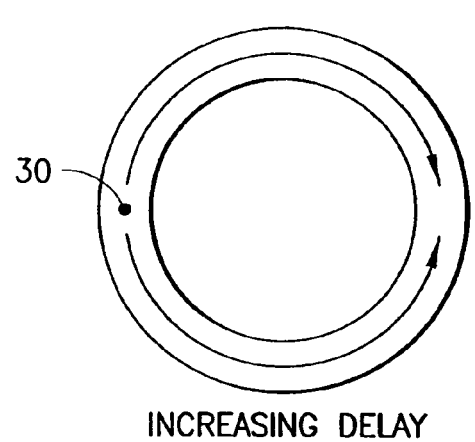
FIG. 25 is a drawing showing increasing delays around an annular ring of subelements with increasing distances from a solitary access switch.
Figure 26:
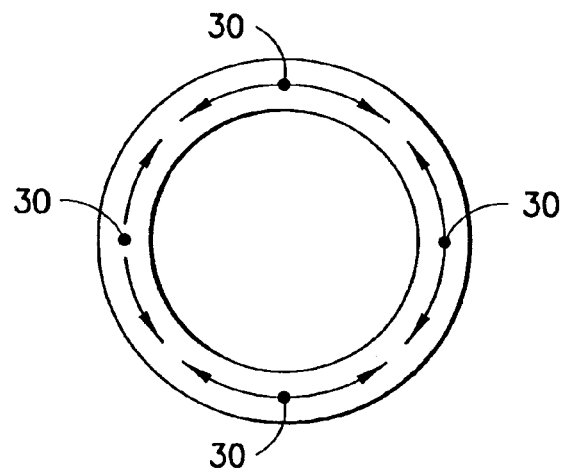
FIG. 26 is a drawing showing increasing delays around an annular ring of subelements with increasing distances from respective access switches placed in each quadrant.
Figure 27:
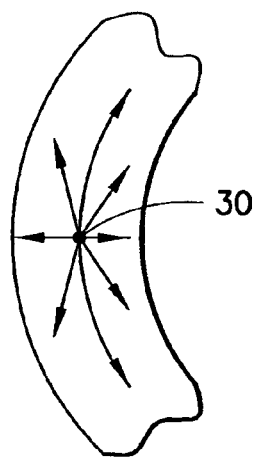
FIG. 27 is a drawing showing increasing delays in an annular ring of subelements with increasing distances from an access switch. The annular ring has a width greater than one subelement.
Figure 28:
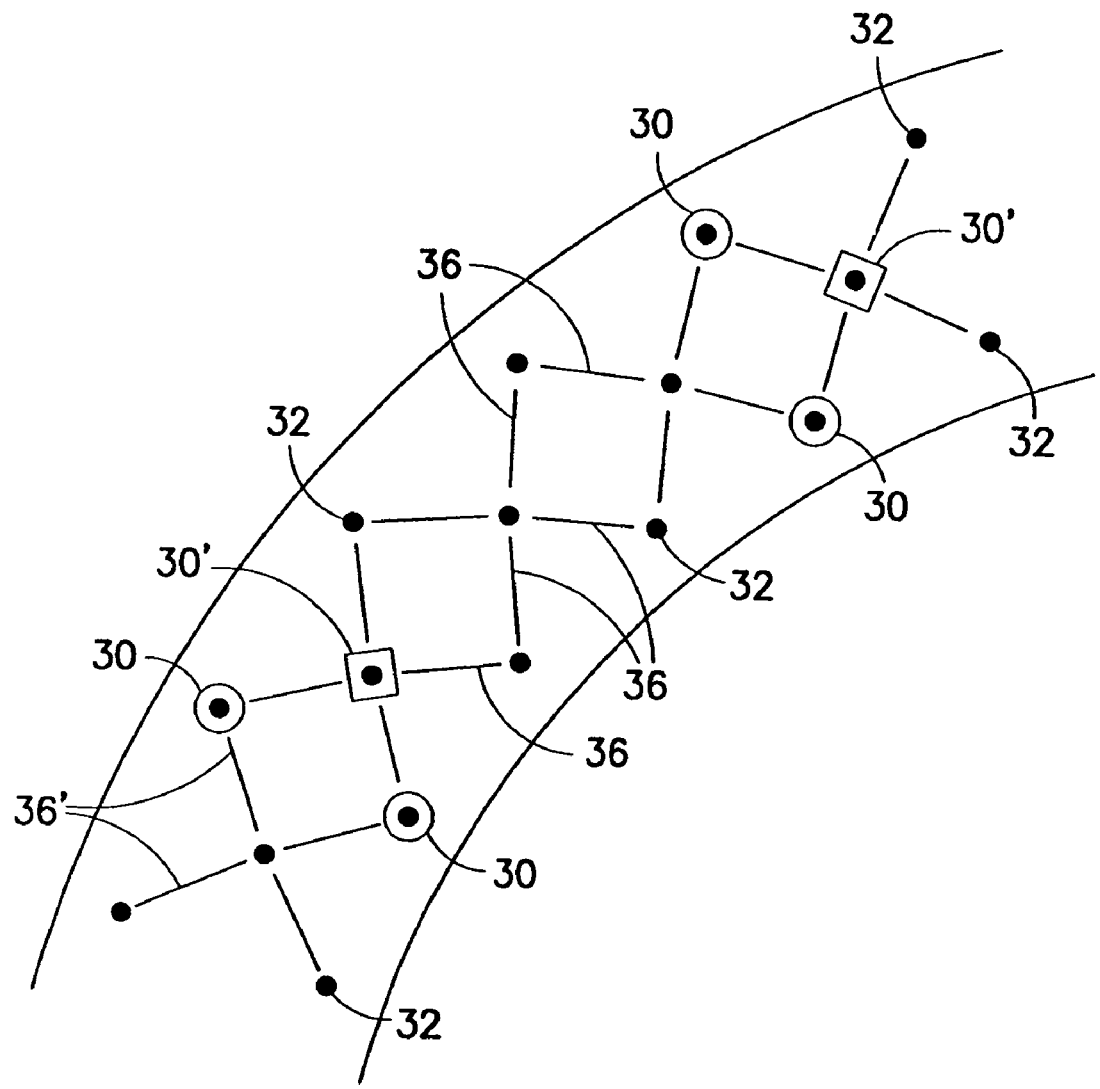
FIG. 28 is a drawing showing a case wherein multiple access switches are used across the width of an annular ring. The solid dots represent acoustical subelements; the circles show the placement of access switches in accordance with one design; and the squares show the placement of access switches in accordance with another design.

In the case of an annular array, the simplest architecture would be as shown in FIG. 25. Here, a single access switch 30 is connected to an entire ring of subelements (individual subelements are not shown), each subelement in turn being connected together by matrix switches (not shown). While simple to implement since it requires only one access switch, this architecture incurs significant delay depending on the size of the matrix switches. Therefore, multiple access switches could be connected to an entire ring as shown in FIG. 26, with matrix switches between subelements (not shown) having access switches 30 to form respective sections of the ring. These access switches would be distributed at equal distances spaced around the ring to reduce the signal delay for those subelements between switches. In this way, multiple redundant matrix switch connections can be employed to form a single ring in order to reduce the series resistance and thereby reduce the delay. As illustrated in FIG. 27, access switches can be chosen to lie equidistant from either edge of a ring to minimize delay inside the ring, if only a single access switch is employed. The edge of the ring refers to the subelement near the inner and outer peripheral borders of the ring. In this way the delay pattern within the ring is improved. If multiple access switches are used across the width of a ring, they should be placed on the inner and outer peripheries of the ring to improve the delay pattern by minimizing the two-dimensional switch distance. FIG. 28 shows such a case. The encircled dots 30 represent access switches arranged in pairs near the inner and outer peripheries of each ring of subelements (individual subelements are not shown). With access switches 30 located on the edges of the ring the signal is driven from both directions and the overall error is reduced. FIG. 28 also shows access switches 30' inside squares and situated in the center of the ring (i.e., midway between the inner and outer peripheral boundaries of the ring). This leads to large errors at the edge of the rings because the access switches do not drive the ring from both edges.

While the present architecture is targeted towards the mosaic annular array concept, it should be clear to those skilled in the art that, patterns other than rings could be formed while still choosing access switch placement to minimize delay. Therefore the invention as described here is directly applicable to other types of imaging, including phased array, linear and two-dimensional arrays.

The method of the present invention can be used to choose the switching configuration that minimizes the errors introduced by the complex switching network. The goal is to reduce the error in such a way that the beamforming is least compromised. There is a multitude of ways in which this can be achieved. Some more specific implementations of algorithms that try to achieve this end are given hereinafter. These implementations should not be viewed as limiting the invention, but rather as examples used to illustrate the potential of such algorithms.

For example, if a complete model of the system is available, then the model can be used to determine the best configuration for the switch network. This could be achieved by generating a switching configuration through some random or semi-random process. The switch configuration is then the input to the model. The model calculates the response of the system taking into account all of the switching network errors. Some form of image or radiation pattern can be generated using the model and certain criteria or cost functions are then calculated based on this data. The result of the cost function is used to modify the configuration. An iterative algorithm is then created, and simulated annealing or some other computational method is used to try and minimize the cost function.

The parameters that are calculated depend on the complexity of the model that has been chosen and the specific cost function which is chosen to be minimized. A thorough model would be able to calculate the acoustical output (pressure as a function of space and time) at the face of the transducer given a particular switching configuration and input excitation. Such a model would need to include the effects of the switching network and the response of the individual transducer cells. Given the acoustical output, there are many cost functions that could then be evaluated. For example the beamwidth of the resulting radiation pattern could be minimized while simultaneously minimizing the sidelobe levels of the pattern. In this case, the model would need to calculate the beamwidth and the sidelobe levels.

Alternatively, if the hardware is available, this optimization process could be done using the actual hardware. In this case the configurations would be generated and applied to the system controller. An image would be made or simplified data taken. Again a cost function would be based on this data and used to modify the configuration. In this case however, there is no modeling involved. One might also evaluate the performance by measuring voltages directly on the underlying CMOS electronics using a probe array designed to match the switching array. Here the speed at which the switching network can be programmed and the speed at which data could be collected and processed limits the number of configurations that could be studied. However, this number is probably quite large and this might be a good way to determine the actual response without forming an image.

In some cases, the complete modeling of the acoustic response of the system, including all of the switching topology errors, is difficult and computationally expensive. Also a working hardware prototype may be unavailable for use in collecting data on the configurations. Even if the hardware were available, the time required to collect and process the data for many configurations would be large. So in order to determine the effectiveness of using this type of algorithm, a simpler model, based on intuition and understanding of how the network might affect the acoustic response, may be employed that allows one to very quickly evaluate many configurations. For instance, it is known that the greater the number of switches through which the signals must pass, the greater the delay and distortion that will be introduced.

It turns out that to first order, a good way to try and arrange the switching network is such that the distance between a connection and a subelement is as small as possible. Here a connection is defined as an access switch, which is on and thus connecting the subelement with the switch directly to the row bus line for a particular channel. And distance refers to the number of switches that a signal must travel through to get from the acoustical subelement to the row bus line. In addition, the connected access switches should be spread out as much as possible to avoid local short distance at the cost of very long runs for some subelements. So the simplified model uses the number of matrix switches through which a signal must travel as a metric for the performance of the configuration. While this is not entirely accurate, this simple model has been shown to improve switching network performance in simulation. This is despite the fact that a two-dimensional phenomenon is being modeled with a one-dimensional metric.

For the particular implementation of the reconfigurability disclosed herein, there are limitations imposed by the electronics. There is a set of rules that governs the switching configurations for a system. In addition to the hard rules, there are the guiding principles such as reducing the distance between an acoustical subelement and a connection point. The rules must be obeyed and the guiding principles can be used to improve performance. The rules are as follows:

[1] Each row has "n" row bus lines. For the example disclosed herein, n=4. This means that for the entire row, there are only four system channel bus lines to which the access switches can connect.

[2] Each subelement in the row connects to only one of the n row bus lines. This follows from the fact that there is only a single access switch in the subelement. This also means that a given subelement can only be directly connected to a single system channel, with that channel being determined by the multiplexer between the system channel bus lines and the row bus lines.

[3] Each row bus line is connected to a single system channel bus line. While the system channel bus lines are multiplexed to the row bus lines, this connection cannot change for a given configuration.

[4] The pattern of which row bus line is connected to a given access switch repeats over the row. For the case described herein, the pattern repeats every four subelements.

[5] For a given circuit implementation, the total number of access switches connected to the same row bus line is a small finite number. In the particular case discussed later in this disclosure, the limit is four. This results from current draw limitations that are imposed by the limited size of the row bus lines. The limit is based on simulations and can be increased by increasing the size of the row bus lines, thus enabling larger current draws, but this might require larger subelements.

The guiding principles have been discussed above, but will be described more concretely hereinafter. In accordance with one embodiment of the invention, the goal is to minimize the delay error introduced by the switching network. This can be done by keeping the distance from a connection point to a subelement as small as possible. In this context, a connection point is a subelement in which the access switch is on. In addition, it is better to have the connection points evenly distributed.

Determining the switching network configuration entails determining which access switches are on and how the multiplexer (meaning the bank of multiplexer switches 40 partly depicted in FIG. 13) between row bus lines and system channel bus lines is set. The matrix switch states are easy to determine, once the desired pattern is known. The matrix switches are set by simply determining if the neighboring subelement, to which the switch connects, should be on the same system channel or not. So the work is determining how to connect system channels to the multiplexed row bus lines. Once this is known, the access switches are also easy to assign.

Determining an optimal switch configuration is more difficult. To get started, a simple algorithmic approach to assigning switches was developed. The algorithm was designed with some of the rules and guiding principles in mind, but is by no means an optimal solution, but rather just a solution to benchmark against. The sought solution is based on the particular desired configuration. In one example, the desired configuration was a 20-ring, equal-width annular array. The algorithm is as follows:

Starting at one edge of the array, work from row to row across the array. For each row and for each bus line on that row:

[1] Determine which rings (i.e., which system channels) are possible for the given row bus line. For example, near the top of the array only the outer element may be present. In that case only the single ring is possible. As one moves toward the center, all of the rings are present, but for a given row bus line only some of the rings will be possible.

[2] For each ring, determine how many access switches could be turned on for the given row bus line, if the multiplexer set that row bus line to the system channel corresponding to that ring.

[3] Assign the row bus line to the ring that would allow the most access switches to be on. However, this should be done subject to the following restraints:

[a] the same ring cannot be assigned to more than one bus line in a row; and

[b] the same ring cannot be assigned to the row bus line if it has already been assigned in the past four rows.

In some cases it is not possible to meet condition [b] and still assign a ring to the particular row bus line. For example, if only three rings are candidates for being assigned to a particular row bus line, but those three rings have just been assigned to the previous three row bus lines, there will be no ring that can be assigned to this particular row bus line. In this case and in all cases were condition [b] prevents a row bus line from being connected to any ring, the limiting condition must be removed. For this algorithm the limitations can be removed in a way that least disrupts the algorithm's intention. So if condition [b] cannot be met, then one by one, remove the restriction of rows starting with the furthest row. So if [b] cannot be met, allow the row bus line assignment to be the same ring assigned to the fourth previous row bus line. If this still does not allow an assignment, allow the row bus line assignment to be the same as the third previous row bus, etc. until the row bus line can be assigned.

The foregoing algorithm can be used to assign multiplexer and access switch settings for a particular desired ring geometry. Because it tries to maximize the number of active access switches, it helps to reduce the distance between a connection point and a subelement. This algorithm is a useful benchmark.

Given a switching network configuration, it is not trivial to determine how effective that configuration will be in an imaging situation. The ultimate gold standard, which should be used to determine if one configuration is better than another, is the quality of the images that such a configuration produces. However, in the absence of a working prototype, this is nearly impossible to do. Also, determining image quality is a difficult metric and even with a working prototype, this could not be used to screen out every possible configuration because of the time and effort that this might require. Given a particular configuration, it is possible to simulate beam profiles using a complete computer model of the electronics. However, this simulation would be very time consuming and should be reserved for only a few configurations and not for a large screening process. It is also possible to simulate only the delay and amplitude changes using a simplified electrical model and then use these as inputs to a simpler beamformer model, but this again takes more time than desired for screening the large number of inputs that are required. A slightly faster method would be to use simplified equations to estimate the delays and then use the simpler beamformer model, but this is still not a very fast simulation that would allow significant screening of many possible configurations.

A method that allows very quick evaluation of many configurations is to assume that the major effect on the delays results from the distance from the subelement to the connection point. Calculating the distance from each subelement to the closest connection point can be made very quickly using lookup tables. This allows an iterative algorithm to be designed that can search through a large number of configurations. While the present invention is not limited to this implementation, the speed of this evaluation is an important advantage that allows practical use of the optimization.

An iterative algorithm was developed that results in great improvement in the delay error over the simple method for determining the switch configuration already described. The algorithm works as follows:

[1] An initial configuration is given. In one case, the output of the simple algorithm was used. This could also be a random configuration.

[2] For the particular geometry, a lookup table (LUT) is generated. This LUT gives the distance in switches from any subelement in a ring to any other subelement in the ring. To improve the speed of calculation of the LUT, some maximum distance is used such that any distance greater than that maximum is simple labeled as larger than the threshold and not calculated.

[3] For the current configuration, the algorithm does the following:

[a] Calculate the distance (number of switches) from each subelement to the closest connection point, using the LUT.

[b] Sort the distances and keep subelements that have the M worst (i.e., largest) distances. In one case, M=10, so the ten worst distances were retained.

[c] Randomly choose one of the subelements that has one of the M worst distances. In this case, a random integer between 1 and 10 was generated to choose the subelement.

[d] Turn on the access switch for the randomly chosen subelement. This will most likely involve turning off other access switches and changing the multiplexer between the system channel bus lines and the row bus lines on the row of that subelement.

[e] Evaluate a global cost function for this newly created configuration. The specific cost function that was used was the number of subelements that had switch distances greater than a threshold. The threshold that was used was four, based on some simulations with single lines of the switches.

[f] If the cost function is less than the cost function of the unchanged configurations, the new configuration is adopted as the current best.

[g] If the cost function is greater with the changed switch, then it may still be kept. This is a simulated annealing type of algorithm. A temperature function is defined and slowly over many iterations the temperature is reduced. Initially, the temperature function is high and thus the likelihood of keeping a configuration despite its larger cost function is greater. As the number of iterations increase, the temperature is lowered and the probability of keeping an inferior configuration is reduced. This type algorithm allows the system to jump out of local minima and thus gives it a chance to find a better (perhaps not global) minimum.

[h] The process repeats for some predetermined number of iterations or until all the distances are below the threshold.

Simulated annealing is a well-known computational method for optimizing a choice of parameters when an exhaustive search of the possible settings is not feasible. Annealing refers to a physical process where by metals crystallize as they cool. The end state of this cooling process depends on the speed at which things were cooled. If the cooling occurs very slowly the system is able to reach a minimum energy state. If things are cooled very quickly, only a local minimum in the energy is achieved. Simulated annealing is a mathematical algorithm which mimics the cooling process. A cost function is defined for the process which you are trying to study and the simulated annealing algorithm attempts to minimize this cost function. Here the cost function is analogous to energy in the physical process of annealing. The simulated annealing algorithm starts with a particular configuration. Random changes to the configuration are made (i.e. random changes in the parameters being optimized are made). These changes may need to follow certain laws or rules. After the changes are made in the configuration the cost function is evaluated again. If the cost function has decreased, the configuration is changed to the new configuration. If the cost function is higher then the configuration may or may not change depending on some random variable's value. As the algorithm progresses the likelihood that the higher cost configuration will be kept is reduced. But by allowing higher cost configuration to occur, the algorithm can avoid local minima and get closer to a more absolute minimum. The probability that a higher cost configuration will be kept is initially high and decreases as the algorithm progresses. This probability is analogous to the temperature in physical annealing. The rate at which the probability is dropped determines the speed of the algorithm. If the rate is high the answer comes quickly but may not be near the true minimum. If the rate is low, the answer takes longer but is more likely to be a minimum.

A switching configuration was determined using the simple algorithm for a mosaic annular array. For the simple algorithm, 172 out of 7015 subelements had a distance of greater than four switches. This means that over 97.5% of the subelements were below the threshold. Using this configuration as the input to the iterative algorithm, a new switching configuration was determined. In this case only 12 out of the 7015 subelements had more than four switches to travel to a connection point, i.e., more than 99.8% of the elements were below the threshold. The 12 subelements that did not meet the threshold criteria were all at a distance of five switches. This shows the improvement over the simple algorithm by reducing those subelements that do not meet the threshold criteria from 172 to 12. However, the iterative algorithm does not take into account the rule that limits the system to four active access switches per row bus line. An additional processing step was used to remove the extra switch. This process removes them in a way that tries to minimize the increase in average distance. The results with these extra switches removed were a great improvement over the simple algorithm. Most of the extra switches were removed near the top and bottom, where the density of connections is large and so little is lost.

The distances were compared to actual delays derived from electronics simulations. Having generated a switching configuration using the iterative algorithm, it is possible to simulate the delays using a simplified model and electronic simulation software (such as HSPICE). This more accurately reflects the two-dimensional nature of the delay problem, which was reduced to a single scalar for computational speed. The results of the simulation of the delays for the same switch configuration using a commercial electronic simulation package were that the peaks in the actual delays always occurred at a peak in the distance metric (which was used to optimize). This evidences the fact that the distance metric is a good metric to use for optimization. There were, however, some peaks in the distance metric that did not have corresponding peaks in the delay. This has to do with the two-dimensional nature of the delays versus the one-dimensional nature of the distance metric.

The above-described switch matrix realization was the output of the iterative algorithm. However, the outcomes can be different for different runs and also depends on the temperature parameters used and the threshold and cost function. It may be possible to improve on the current design with more optimization time. It should also be noted that this is just one exemplary algorithm for minimizing errors. Others could also be used to improve performance.

To form a linear scan, the active aperture of the mosaic annular array must be stepped across the underlying two-dimensional array. This stepping requires that the switching network be reconfigured. There are several ways in which this stepping can be done. If the required beam spacing, as determined by the resolution of the array and the requirements of the application at hand, is such that stepping an entire subelement is acceptable, then the same algorithmically derived switch configuration can be used for each beam. In this case the switching configuration simply steps over one or several subelements for each beam. In order to minimize the reprogramming and power used by the system to reconfigure, it may be possible to transfer switch states directly from one subelement to the neighbor and thereby avoid reprogramming the entire array externally. However, in addition to translating the access and matrix switch pattern, the multiplexer connecting the row bus lines to the system channel bus lines must also be changed. When stepping the beam by entire subelements in the direction of the row bus lines this change is simply a rotation of the channels. For example, if four system channels, designated A, B, C, and D respectively, are connected to the four row bus lines of a particular row for a particular configuration, when the switching pattern is scanned to the next beam location, the state of the system channel/row multiplexer must be adjusted so that the system channels rotate among the four row bus lines, e.g., system channels B, C, D, and A are connected in that order to the same four row bus lines respectively. Alternatively, rather than change the multiplexing between system channels and row bus lines, the system beamformer could take into account the change in geometry directly and therefore adjust the delays on the four channels to take into account the new delays.

As mentioned above, if the annular rings are stepped such that the motion is an integer multiple of the subelements there is no need to re-optimize for each beam (assuming that the underlying switch matrix has uniform electrical properties across the entire underlying two-dimensional array). However, there may be cases in which the desired beam density calls for lines to be closer together than a single subelement. In this case the beam center is stepped a fraction of a subelement, e.g., the aperture is deformed to effectively steer the beam a half step between full steps of the aperture, thereby increasing the resolution of the imager. For these cases the optimization does not simply translate and a new optimization must be run for each fractional step. However, these fractional stepping configurations may re-occur as the annular array is stepped across the underlying two-dimensional array to form a linear scan. In these cases, wherever the same fractional step is required, the optimization will be the same and can be re-used. So even in the case of fractional stepping, there will be a small number of optimizations required. In these cases, to save programming time and power consumption, it may be possible to fire all the beams for a particular configuration and step that configuration across the array at the coarse beam spacing. In this case it would be possible to pass configurations from subelement to neighbor directly. After the coarse scan has been completed, a new configuration which represents a fractional step from the old configuration can be programmed and stepped across the array. This can be repeated for each fractional step. The resulting coarsely spaced beams from each configuration can be interleaved by the scan converter to give the desired fine beam spacing. It should also be noted that when mixing beams from different configurations, it may be necessary to adjust the gain from beam to beam to compensate for beamforming gain differences and to blend the lines from those different configurations.

The numerical optimization algorithm disclosed hereinabove improves the beamforming performance of a reconfigurable array. The problem to be solved was that, in the case of simplified switching networks for reconfigurable arrays, delays, amplitude changes, and waveform distortion all occur due to the simplified switching network. The use of numerical optimizations can help to minimize the error and maintain adequate beamforming performance. A specific example of such an optimization was explored in which a simple metric was defined and used to characterize the performance of the various configurations. The simple metric used in the example was the number of switches between a given subelement and the closest access switch that was connected (i.e., in a closed state) to a row bus line. The results obtained showed that this simple metric can improve the performance of the switching network despite the crude approximations made. The simple metric also allows many configurations to be explored, which increases the chances for success.

The optimization technique disclosed herein provides improved imaging performance with the simplified switching networks for reconfigurable arrays. The reduction in delay errors and distortions leads directly to improved beamforming, including improved resolution and contrast.

The optimization algorithm can be used with either a full or a sparse multiplexer. The algorithm could generate its data ahead of time for storage and later use or it could be generated locally during imaging for incremental improvements due to changes in the array resistances. The algorithm could be done during the design phase assuming ideal resistance values, at the time of manufacture using the actual resistance values as measured, or periodically in the field (e.g., every time the ultrasound imaging machine is turned on, or during use, whenever it is determined that calibration needs to be done or whenever the array configuration is changed) as a calibration step to be used as the system ages or to compensate for variations due to temperature. For example, the system could be automatically calibrated in response to detection of a predetermined change in temperature. In addition, variations in fabricated cMUT capacitances would also affect the array performance. These variations could be accounted for by repeating the optimization procedure after the exact cMUT capacitance for every subelement in the fabricated array has been measured.

Calibration data is unique to each probe and could be stored with each probe in a ROM or EPROM, or it could be stored on the imaging system as a file that is downloaded to the probe over a data link in the cable, to be stored locally in a RAM, EEPROM, FRAM, etc. in the probe itself. This data would then be read out from the local (probe) memory during scanning with each new scan reading the new required configuration data. Alternatively, calibration data could be calculated during system use and then downloaded to the probe.

The incorporation of access and matrix switches for connecting sensor elements to bus lines provides great flexibility. In accordance with various embodiments of the invention, one or more of the following features can be employed:

(1) The access switches can be staggered to reduce the number of access switches required for a given number of bus lines.

(2) A single access switch can be used for a subelement in a staggered pattern.

(3) A random ordering of access switch to bus line mapping can be employed to reduce artifacts due to the repeating patterns.

(4) More than one access switch can be used in each subelement, but still fewer than the number of bus lines and system channels.

(5) Bus lines can be connected to system channels using a cross-point switching matrix.

(6) A sparse cross-point switch can be used to connect bus lines to system channels.

(7) Switches can be configured to ensure that there is a respective different access switch connected at both ends of a long run of matrix switch connections, which access switches are connected to the same bus line, to reduce delay.

(8) Switching configurations can be employed in which there are a set of matrix switches and a limited number of access switches. The matrix switches connect neighboring subelements dynamically. The access switches connect to bus lines that are multiplexed to system channels.

In accordance with various embodiments of the invention, one or more of the following additional features can be present in the system:

(1) One access switch per bus line is used in each subelement.

(2) Multiple bus lines can be used per row.

(3) The bus lines can be disposed both vertically and horizontally within an array. In accordance with one embodiment, if one set of bus lines is disposed horizontally and another set is disposed vertically, each subelement or group of subelements will be connectable to a vertical bus line via one access switch and will further be connectable to a horizontal bus line via a different access switch. However, in the case where bus lines are run in both directions because the electronic real estate available for bus lines is running low and more bus lines are needed, but there is still only a single access switch in a subelement, then each subelement's access switch could be connected to either the horizontal bus line or the vertical bus line and not both. This also has implications when the number of switches that can be on for a given bus line is limited by current draw and the size of the line.

(4) Access switches can be chosen to lie equidistant from either edge of a ring (or other shape) to minimize delay inside the ring. An "edge of a ring" refers to the case in which the reconfigurability is used to approximate an annular array. In this case there is some desired annular array or ring structure that one wants to mimic by connecting subelements. The edge of the ring refers to the subelement near the border of the ring that one is trying to approximate, i.e., it is the edge of the larger element which is formed by connecting subelements. The access switches should be chosen to be on both sides of the element, not all on one side. The shape need not be a ring; instead other shapes could be used, and it would be best to have access switches on both edges of the shape that is approximated by connecting the subelements.

(5) More than one access switch per bus line could be used in each subelement. This redundant connection improves device yield.

(6) One could provide the ability to update ring patterns between transmit and receive and at multiple intervals during receive.

(7) A single access switch could be connected to an entire ring of subelements, each subelement in turn being connected together by matrix switches.

(8) Multiple access switches could be connected to an entire ring, with matrix switches between subelements having access switches to form respective sections of the ring.

(9) Multiple access switches could be connected to an entire ring, with the switches being distributed at equal distances spaced around the ring to reduce the signal delay for those subelements between switches

(10) Multiple rings can be formed, wherein each ring is connected to a single system channel using one or more access switches, each of which is connected to a bus line, which is in turn connected to a system channel.

(11) Multiple redundant matrix switch connections can be employed to form a single ring in order to reduce the series resistance and thereby reduce the delay.

(12) Matrix switches can be used to route around a known bad subelement for a given array.

(13) Patterns other than rings can be formed while still choosing access switch placement to minimize delay.

(14) An entire ring pattern can be translated to create a moving beam by repeated use of the minimum delay algorithm at each new step in the translation.

(15) The center of an element can be stepped by an increment less than a complete subelement by changing the shape of the element.

The switching electronics can be built using CMOS or BiCMOS, or SOI, or MEMS or other as yet unidentified switching technology.

While the invention has been described with reference to preferred embodiments, it will be understood by those skilled in the art that various changes may be made and equivalents may be substituted for elements thereof without departing from the scope of the invention. In addition, many modifications may be made to adapt a particular situation to the teachings of the invention without departing from the essential scope thereof. Therefore it is intended that the invention not be limited to the particular embodiment disclosed as the best mode contemplated for carrying out this invention, but that the invention will include all embodiments falling within the scope of the appended claims.

The invention claimed is:

1. A method for implementing a switching configuration that minimizes the errors introduced by a network of switches during control of a reconfigurable array of sensor elements, comprising the following steps:

(a) generating an initial switching configuration; and (b) performing an iterative algorithm comprising the following steps:
(i) inputting a switch configuration into a model of the system that calculates the response of the system, taking into account all of the switching network errors, said initial switching configuration being inputted at the start and successively derived modified switching configurations being inputted in succession thereafter;
(ii) generating an image or radiation pattern using the model with the inputted switch configuration;
(iii) calculating a value for a cost function based at least in part on data representing the generated pattern;
(iv) determining whether the calculated value substantially represents a minimum for said cost function; and
(v) if the calculated value is not a minimum for said cost function, modifying the current switching configuration as a function of the results of said value calculation to arrive at a modified switching configuration, steps (i) through (v) being repeated for each switching configuration; and
(c) if the calculated value is a minimum for said cost function, configuring said switching network with the modified switching configuration that caused the cost function value to be minimized.

2. The method as recited in claim 1, wherein said configuring step comprises programming control circuitry for controlling the states of the switches.

3. The method as recited in claim 1, wherein the step of determining whether the calculated value substantially represents a minimum for said cost function is performed using a simulated annealing type of algorithm.

4. The method as recited in claim 1, wherein the cost function used is the number of sensor elements having switch distances greater than a predetermined threshold.

5. The method as recited in claim 1, wherein the cost function used changes with application.

6. The method as recited in claim 5, wherein a first cost function is used for optimizing a first switching configuration for use when the array of sensor elements is operated in a transmit mode, and a second cost function is used for optimizing a second switching configuration for use when the array of sensor elements is operated in a receive mode.

7. The method as recited in claim 5, wherein a first cost function is used for optimizing a first switching configuration for use when the array of sensor elements is operated in accordance with a first set of system parameters, and a second cost function is used for optimizing a second switching configuration for use when the array of sensor elements is operated in accordance with a second set of system parameters.

8. The method as recited in claim 1, wherein said method is performed whenever the configuration of the array of sensor elements changes.

9. The method as recited in claim 1, wherein said method is performed whenever a predetermined temperature change in the operating environment of the array of sensor elements is detected.

10. The method as recited in claim 1, wherein the array of sensor elements is coupled to an imaging system, and said method is performed whenever the imaging system is turned on.

11. The method as recited in claim 1, wherein the array of sensor elements is incorporated in a probe that can be coupled to an imaging system, and data representing said modified switching configuration that caused the cost function value to be minimized is stored in memory in the probe.

12. The method as recited in claim 1, wherein the array of sensor elements is incorporated in a probe that can be coupled to an imaging system, and data representing said modified switching configuration that caused the cost function value to be minimized is stored in memory in the imaging system and later downloaded to local memory in the probe.

13. The method as recited in claim 1, wherein data representing said modified switching configuration that caused the cost function value to be minimized is read out from the local memory in the probe during scanning.

14. The method as recited in claim 1, wherein said method is performed during the design phase assuming ideal resistance values for the switches.

15. The method as recited in claim 13, wherein each sensor element is a respective ultrasonic transducer element, and said method is performed during the design phase assuming ideal capacitance values for the ultrasonic transducer elements.

16. A method for implementing a switching configuration that minimizes the errors introduced by a network of switches during control of a reconfigurable array of sensor elements, comprising the following steps:
(a) generating an initial switching configuration; and
(b) performing an iterative algorithm comprising the following steps:
(i) inputting a switch configuration into a system, said initial switching configuration being inputted at the start and successively derived modified switching configurations being inputted in succession thereafter;
(ii) determining the performance of the system with the inputted switch configuration;
(iii) calculating a value for a cost function based at least in part on data representing the determined performance of the system;
(iv) determining whether the calculated value substantially represents a minimum for said cost function; and
(v) if the calculated value is not a minimum for said cost function, modifying the current switching configuration as a function of the results of said value calculation to arrive at a modified switching configuration, steps (i) through (v) being repeated for each switching configuration; and
(c) if the calculated value is a minimum for said cost function, configuring said switching network with the modified switching configuration that caused the cost function value to be minimized.

17. The method as recited in claim 16, wherein said configuring step comprises programming control circuitry for controlling the states of the switches.

18. The method as recited in claim 16, wherein the step of determining whether the calculated value substantially represents a minimum for said cost function is performed using a simulated annealing type of algorithm.

19. The method as recited in claim 16, wherein the cost function used is the number of sensor elements having switch distances greater than a predetermined threshold.

20. The method as recited in claim 16, wherein step (b)(ii) comprises the step of calculating a radiation pattern of said system.

21. The method as recited in claim 16, wherein step (b)(ii) comprises the step of evaluating an image produced by said system.

22. The method as recited in claim 16, wherein step (b)(ii) comprises the step of making electrical measurements of said system.

23. The method as recited in claim 16, wherein each sensor element is a respective ultrasonic transducer element, and step (b)(ii) comprises the steps of measuring the on resistances of the switches and measuring the capacitances of the ultrasonic transducer elements.

24. The method as recited in claim 16, wherein the cost function used changes with application.

25. The method as recited in claim 24, wherein a first cost function is used for optimizing a first switching configuration for use when the array of sensor elements is operated in a transmit mode, and a second cost function is used for optimizing a second switching configuration for use when the array of sensor elements is operated in a receive mode.

26. The method as recited in claim 24, wherein a first cost function is used for optimizing a first switching configuration for use when the array of sensor elements is operated in accordance with a first set of system parameters, and a second cost function is used for optimizing a second switching configuration for use when the array of sensor elements is operated in accordance with a second set of system parameters.

27. The method as recited in claim 16, wherein said method is performed whenever the configuration of the array of sensor elements changes.

28. The method as recited in claim 16, wherein said method is performed whenever a predetermined temperature change in the operating environment of the array of sensor elements is detected.

29. The method as recited in claim 16, wherein the array of sensor elements is coupled to an imaging system, and said method is performed whenever the imaging system is turned on.

30. The method as recited in claim 16, wherein the array of sensor elements is incorporated in a probe that can be coupled to an imaging system, and the data representing said modified switching configuration that caused the cost function value to be minimized is stored in memory in the probe.

31. The method as recited in claim 16, wherein the array of sensor elements is incorporated in a probe that can be coupled to an imaging system, and the data representing said modified switching configuration that caused the cost function value to be minimized is stored in memory in the imaging system and later downloaded to local memory in the probe.

32. The method as recited in claim 16, wherein the data representing said modified switching configuration that caused the cost function value to be minimized is read out from the local memory in the probe during scanning.

33. The method as recited in claim 16, wherein each sensor element is a respective ultrasonic transducer element, and said method is performed for each of a multiplicity of aperture configurations for reconfiguration at multiple focal zones during a receive mode.

* * * * *